United States Patent [19]
Shalon et al.

[11] Patent Number: 5,793,468
[45] Date of Patent: Aug. 11, 1998

[54] AUTOMATED HAND-HELD KERATOMETER

[75] Inventors: Tadmor Shalon, Brentwood; Marvin L. Pund, Chesterfield, both of Mo.

[73] Assignee: Metaphase Corporation, St. Louis, Mo.

[21] Appl. No.: 488,298

[22] Filed: Jun. 7, 1995

Related U.S. Application Data

[63] Continuation of Ser. No. 775,194, Oct. 11, 1991, Pat. No. 5,585,873.

[51] Int. Cl.$^6$ .................................................. A61B 3/10
[52] U.S. Cl. ........................... 351/218; 351/211; 351/212
[58] Field of Search .................................. 351/206–218, 351/247

[56] References Cited

U.S. PATENT DOCUMENTS

| Re. 27,475 | 9/1972 | Volk | 351/39 |
|---|---|---|---|
| 1,006,825 | 10/1911 | Buchhop . | |
| 1,721,208 | 7/1929 | Currier et al. . | |
| 1,750,931 | 3/1930 | Kellner et al. . | |
| 2,174,308 | 9/1939 | Hartinger . | |

(List continued on next page.)

FOREIGN PATENT DOCUMENTS

3125494 A1  6/1981  Germany .

OTHER PUBLICATIONS

R.E. Frazer, et al., National Aeronautics and Space Administration, "NASA Tech Brief: Real–Time Keratometer", Aug. 1988, 2 pages, Springfield, Virginia, U.S.
Topcon, "Topcon Lensmeter LM–6/LM–6E", 1988 (4 pages).
Topcon, "Lensmeter LM–S1", 1989, (2 pages).
Topcon, "KR–3000 Auto Kerato–Refractometer", 1990, (4 pages).
Terence C. Honikman, Ph.D., "Trends in Iols & Refractive Surgery", Oct. 2, 1985, (9 pages).
Allergan Humphrey, "Humphrey Lens Analyzer", 1989, (2 pages).
Topcon, "Digital Projection Lensmeter LM–P5", 1989, (3 pages).
Marco, "Lensmeter 101 and Lensmeter 201", date unknown, (1 page).
Allergan Humphrey, "Auto Keratometer", 1989, (2 pages).
Marco, "Keratometer I and Keratometer II", 1989 (4 pages).
Topcon, "Computerized Lensmeter CL–2000", 1989, (4 pages).
Marco Technologies, "ARK–2000 Automatic Refractor/Keratometer", date unknown, (2 pages).
Marco Technologies, "LM–870 Automatic Lensmeter", date unknown, (2 pages).

*Primary Examiner*—Thong Nguyen
*Attorney, Agent, or Firm*—Howell & Haferkamp, L.C.

[57] ABSTRACT

An automated portable keratometer includes a hand held housing and is battery powered. A projection system projects collimated light sources at equal converging angles to an optical axis which extends outside the housing. A camera, including an imaging device, and telocentric objective lens are aligned along the optical axis in the housing. The projection system projects a known pattern of collimated light sources onto a patient's eye. The reflected images of these light sources is captured by the camera and imaging device. Derivation of the distances between certain reflected images can be converted by known algorithms into radii of curvature of the eye. Alignment leveling, and other features can be included with the keratometer. The device can also be used to measure other curved surfaces.

32 Claims, 36 Drawing Sheets

U.S. PATENT DOCUMENTS

| | | | |
|---|---|---|---|
| 3,108,523 | 10/1963 | Nuchman et al. | 95/11 |
| 3,141,396 | 7/1964 | Kimball et al. | 95/11 |
| 3,169,459 | 2/1965 | Friedberg et al. | 95/18 |
| 3,248,162 | 4/1966 | Knoll | 351/6 |
| 3,264,932 | 8/1966 | Hendricks | 88/24 |
| 3,404,936 | 10/1968 | Bennett et al. | 351/6 |
| 3,416,855 | 12/1968 | McClernon | 351/6 |
| 3,432,227 | 3/1969 | Soper | 351/13 |
| 3,442,579 | 5/1969 | Friedberg | 351/6 |
| 3,453,437 | 7/1969 | Westheimer et al. | 250/217 |
| 3,486,812 | 12/1969 | Volk | 351/6 |
| 3,487,069 | 12/1969 | Masselli | 250/218 |
| 3,536,384 | 10/1970 | Cocks | 351/6 |
| 3,542,458 | 11/1970 | Volk | 351/39 |
| 3,544,220 | 12/1970 | Kaye | 356/109 |
| 3,552,837 | 1/1971 | Volk | 351/13 |
| 3,572,909 | 3/1971 | Van Patten et al. | 351/6 |
| 3,598,478 | 8/1971 | Townsley | 351/6 |
| 3,634,003 | 1/1972 | Guyton | 351/17 |
| 3,664,631 | 5/1972 | Guyton | 351/27 |
| 3,669,530 | 6/1972 | Guyton | 351/17 |
| 3,797,921 | 3/1974 | Kilmer et al. | 351/7 |
| 3,871,772 | 3/1975 | Munnerlyn et al. | 356/153 |
| 3,879,113 | 4/1975 | Howland et al. | 351/7 |
| 3,883,233 | 5/1975 | Guilino | 351/6 |
| 3,932,030 | 1/1976 | Hasegawa et al. | 351/6 |
| 3,969,019 | 7/1976 | Nohda | 351/13 |
| 3,972,602 | 8/1976 | Inns | 351/6 |
| 4,019,813 | 4/1977 | Cornsweet et al. | 351/14 |
| 4,021,102 | 5/1977 | Iizuka | 351/13 |
| 4,157,859 | 6/1979 | Terry | 350/35 |
| 4,159,867 | 7/1979 | Achatz et al. | 351/6 |
| 4,162,828 | 7/1979 | Trachtman | 351/9 |
| 4,165,744 | 8/1979 | Cravy et al. | 128/303.1 |
| 4,172,639 | 10/1979 | Lang et al. | 351/13 |
| 4,180,323 | 12/1979 | Persson et al. | 356/3 |
| 4,196,980 | 4/1980 | Heine | 351/13 |
| 4,199,816 | 4/1980 | Humphrey | 364/571 |
| 4,220,401 | 9/1980 | Muchel | 351/13 |
| 4,256,385 | 3/1981 | Cohen et al. | 351/13 |
| 4,293,198 | 10/1981 | Kohayakawa et al. | 351/13 |
| 4,293,199 | 10/1981 | Wada et al. | 351/13 |
| 4,304,468 | 12/1981 | Wada | 351/13 |
| 4,312,574 | 1/1982 | Wilms | 351/7 |
| 4,315,672 | 2/1982 | Müller et al. | 351/13 |
| 4,353,625 | 10/1982 | Nohda et al. | 351/13 |
| 4,355,871 | 10/1982 | Nevyas et al. | 351/13 |
| 4,367,019 | 1/1983 | Kitao et al. | 351/211 |
| 4,372,655 | 2/1983 | Matsumura et al. | 351/206 |
| 4,373,787 | 2/1983 | Crane et al. | 351/210 |
| 4,390,255 | 6/1983 | Nohda et al. | 351/212 |
| 4,396,261 | 8/1983 | Herbert | 351/247 |
| 4,407,572 | 10/1983 | Humphrey | 351/212 |
| 4,410,243 | 10/1983 | Fürste | 351/211 |
| 4,420,228 | 12/1983 | Humphrey | 351/212 |
| 4,421,391 | 12/1983 | Matsumura et al. | 351/211 |
| 4,429,960 | 2/1984 | Mocilac et al. | 351/212 |
| 4,440,477 | 4/1984 | Schachar | 351/212 |
| 4,444,476 | 4/1984 | Simon et al. | 351/211 |
| 4,453,808 | 6/1984 | Takahashi et al. | 351/208 |
| 4,491,398 | 1/1985 | Karickhoff | 351/211 |
| 4,529,280 | 7/1985 | Nohda | 351/211 |
| 4,533,221 | 8/1985 | Trachtman | 351/203 |
| 4,540,254 | 9/1985 | Humphrey | 351/212 |
| 4,569,576 | 2/1986 | Karpov et al. | 351/212 |
| 4,572,628 | 2/1986 | Nohda | 351/212 |
| 4,588,270 | 5/1986 | Tamaki | 351/212 |
| 4,597,648 | 7/1986 | Feldon et al. | 351/212 |
| 4,606,623 | 8/1986 | Schachar | 351/212 |
| 4,609,287 | 9/1986 | Kohayakawa | 356/124 |
| 4,637,700 | 1/1987 | Krueger | 351/211 |
| 4,660,945 | 4/1987 | Trachtman | 351/203 |
| 4,660,946 | 4/1987 | Nakamura et al. | 351/212 |
| 4,662,730 | 5/1987 | Outwater et al. | 351/212 |
| 4,692,003 | 9/1987 | Adachi et al. | 351/212 |
| 4,697,895 | 10/1987 | Sekiguchi et al. | 351/243 |
| 4,705,037 | 11/1987 | Peyman et al. | 128/305 |
| 4,710,003 | 12/1987 | Masuda et al. | 351/212 |
| 4,730,917 | 3/1988 | Krueger | 351/211 |
| 4,753,527 | 6/1988 | Ishihara | 351/244 |
| 4,755,043 | 7/1988 | Carter | 351/205 |
| 4,761,070 | 8/1988 | Fukuma | 351/205 |
| 4,761,071 | 8/1988 | Baron | 351/212 |
| 4,768,875 | 9/1988 | Müller | 351/212 |
| 4,772,114 | 9/1988 | Fukui et al. | 351/211 |
| 4,772,115 | 9/1988 | Gersten et al. | 351/212 |
| 4,779,973 | 10/1988 | Miller et al. | 351/212 |
| 4,828,381 | 5/1989 | Shindo | 351/211 |
| 4,848,896 | 7/1989 | Matsumoto | 351/211 |
| 4,863,280 | 9/1989 | Gersten et al. | 351/212 |
| 4,881,807 | 11/1989 | Luce et al. | 351/208 |
| 4,903,706 | 2/1990 | Vila-Cora et al. | 128/745 |
| 5,011,276 | 4/1991 | Iwamoto | 351/211 |
| 5,157,427 | 10/1992 | Humphrey | 351/205 |
| 5,189,449 | 2/1993 | Perkins | 351/211 |
| 5,585,873 | 12/1996 | Shalon et al. | 351/212 |

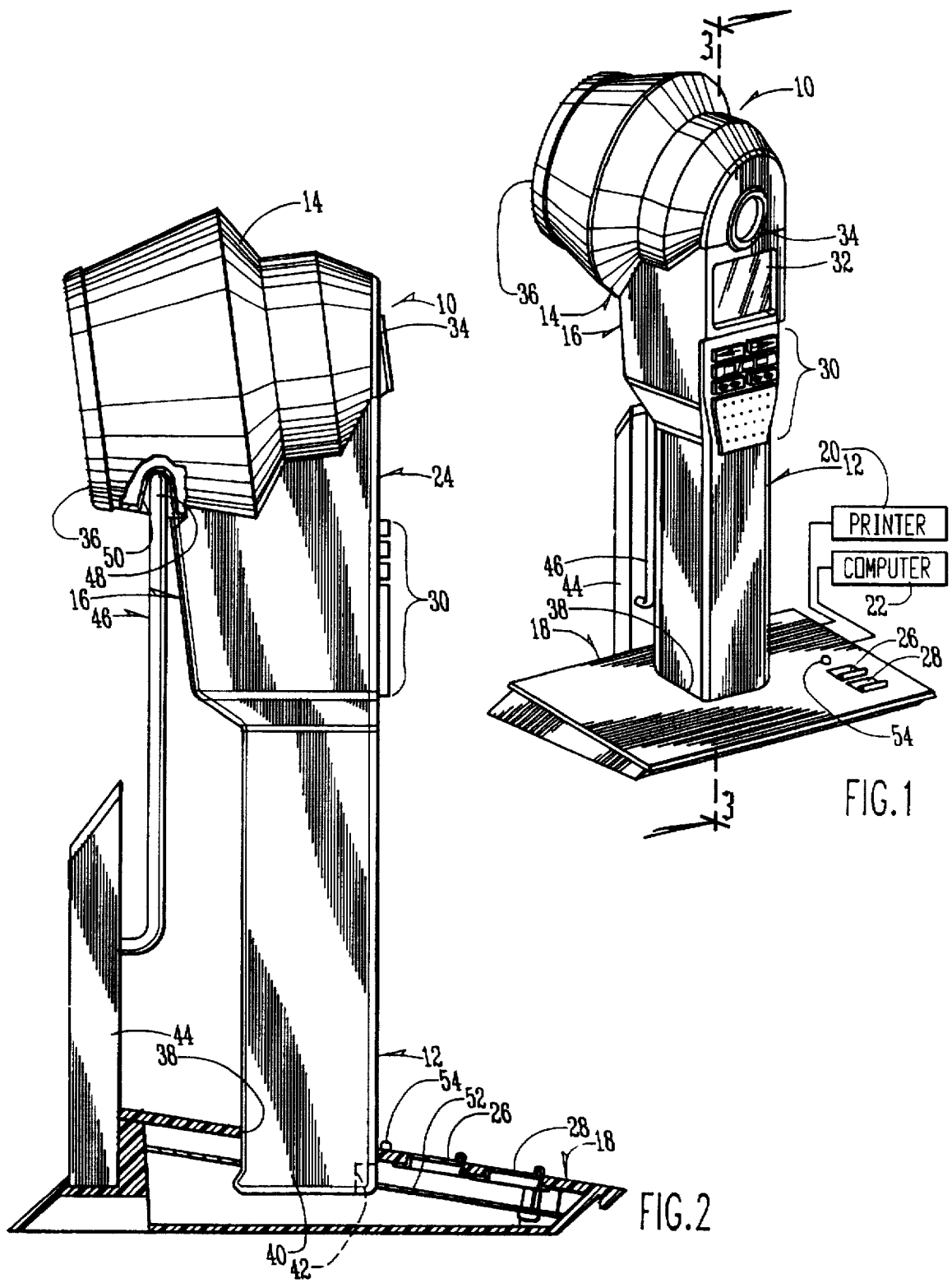

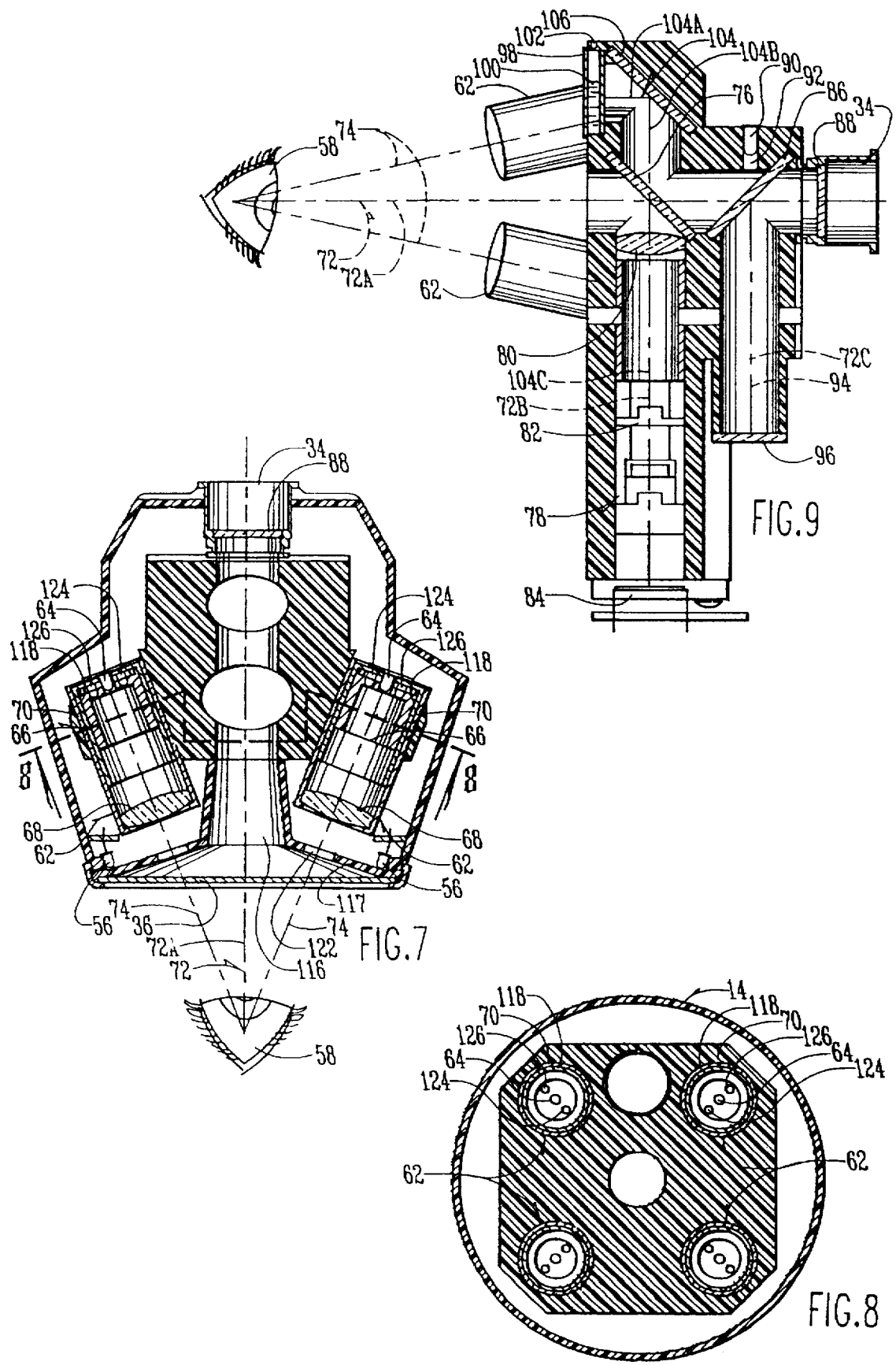

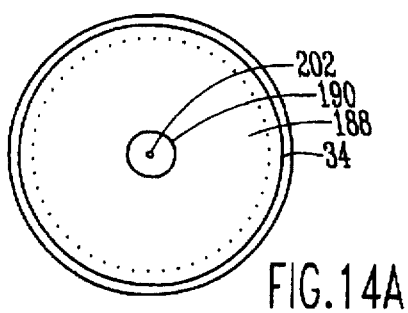
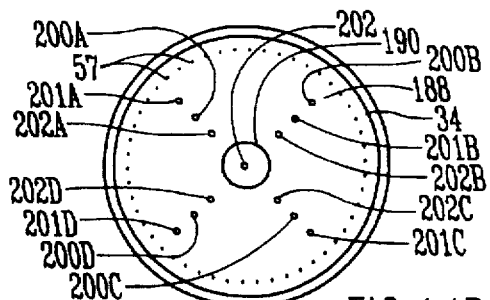
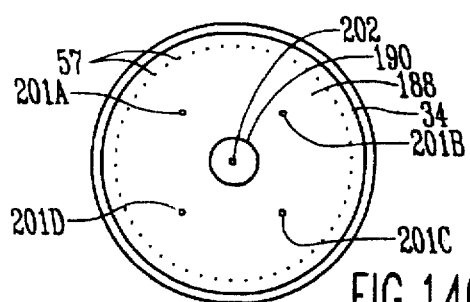
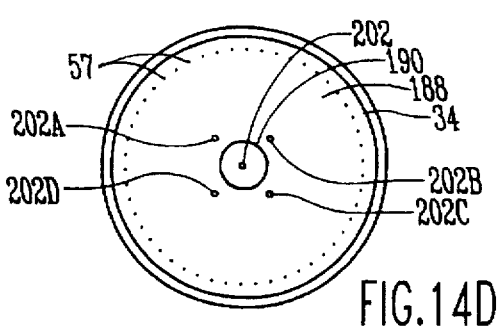
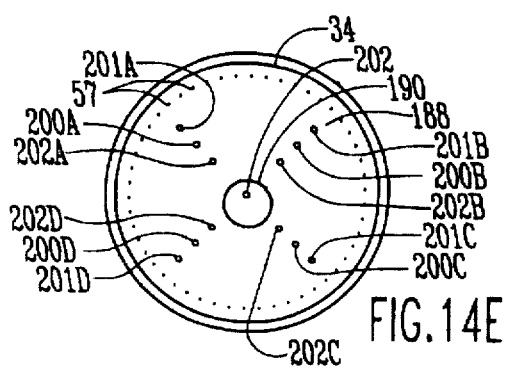
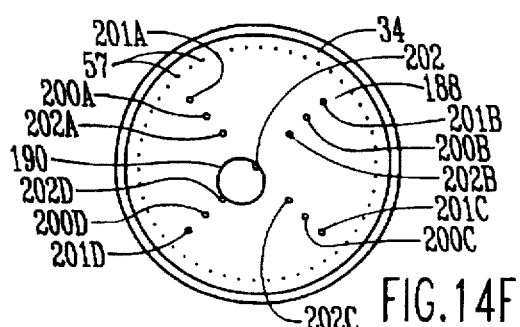
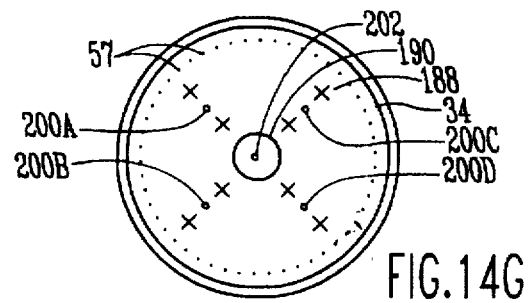
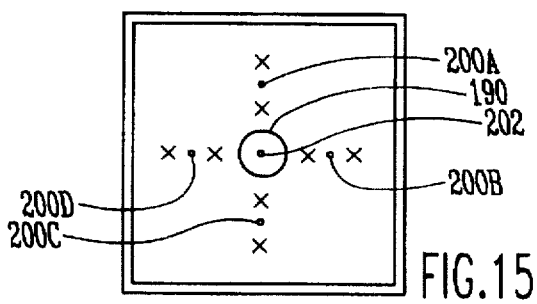

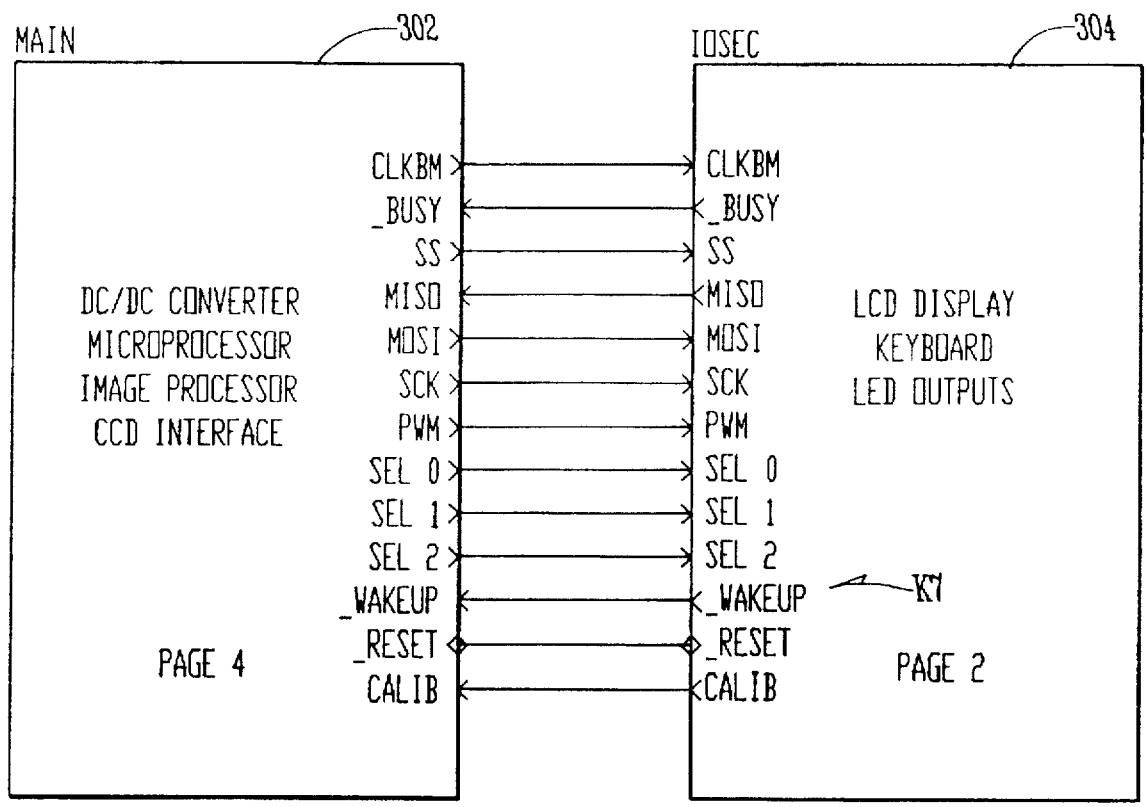
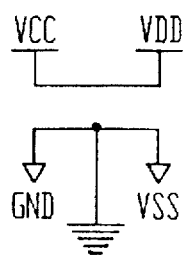
FIG. 17

| EVENTS: / STATES: | NO EVENT | SELECT KEY | SCROLL KEY | CLEAR KEY | RIGHT EYE KEY | LEFT EYE KEY | ALIGN KEY |
|---|---|---|---|---|---|---|---|
| HOLD | DO NOTHING / HOLD | PREPARE FOR DISPLAY MODE / FNE=DISPLAY / SELECT KEY | PREPARE FOR DISPLAY MODE / FNE=DISPLAY / SELECT KEY | PREPARE FOR DISPLAY MODE / FNE=DISPLAY / SELECT KEY | PREPARE FOR DISPLAY MODE / FNE=DISPLAY / SELECT KEY | PREPARE FOR DISPLAY MODE / FNE=DISPLAY / SELECT KEY | PREPARE FOR DISPLAY MODE / FNE=DISPLAY / SELECT KEY |
| DISPLAY | DO NOTHING / DISPLAY | OPTIONS MENU SELECT / OPTIONS | PRINT RESULTS / DISPLAY | CLEAR READING / DISPLAY | SELECT RIGHT EYE / DISPLAY | SELECT DISPLAY / LEFT EYE | MIRE MODE / DISPLAY |
| THRESHOLD | DO NOTHING / THRESHOLD | DO NOTHING / THRESHOLD | DO NOTHING / THRESHOLD | DO NOTHING / DISPLAY | DO NOTHING / THRESHOLD | DO NOTHING / THRESHOLD | DO NOTHING / THRESHOLD |
| MEASURE | DO NOTHING / MEASURE | DO NOTHING / MEASURE | DO NOTHING / MEASURE | POST MEASURING / DISPLAY | DO NOTHING / MEASURE | DO NOTHING / MEASURE | DO NOTHING / MEASURE |
| OPTIONS | DO NOTHING / OPTIONS | OPTIONS MENU SELECT / OPTIONS | OPTIONS MENU SCROLL / OPTIONS | EXIT OPTIONS / OPTIONS | DO NOTHING / OPTIONS | DO NOTHING / OPTIONS | EXIT OPTIONS / HIDDEN / FNE=SELECT KEY |
| HIDDEN | DO NOTHING / HIDDEN | HIDDEN MENU SELECT / HIDDEN | HIDDEN MENU SCROLL / HIDDEN | EXIT HIDDEN / HIDDEN | DO NOTHING / HIDDEN | DO NOTHING / HIDDEN | DO NOTHING / HIDDEN |

FIG. 34B

| MEASURE KEY | PRINT KEY | ON FLAG | REPEAT FLAG | FAILED FLAG | PC MESSAGE | FIELD TEST TERMINAL | TIMEOUT |
|---|---|---|---|---|---|---|---|
| PREPARE FOR DISPLAY MODE / FNE= DISPLAY MEASURE KEY | PREPARE FOR DISPLAY MODE / FNE= DISPLAY PRINT KEY | PREPARE FOR DISPLAY MODE / FNE= DISPLAY ON FLAG | PREPARE FOR DISPLAY MODE / FNE= DISPLAY REPEAT FLAG | PREPARE FOR DISPLAY MODE / FNE= DISPLAY FAILED FLAG | PREPARE FOR DISPLAY MODE / FNE= DISPLAY PC MESSAGE | PREPARE FOR DISPLAY MODE / FNE= DISPLAY FLD TST TERM. | PREPARE FOR DISPLAY MODE / SLEEP |
| PRE THRESHOLDING / THRESHOLD | PRINT RESULTS / DISPLAY | DO NOTHING / DISPLAY | DO NOTHING / DISPLAY | DO NOTHING / DISPLAY | COMMAND FROM PC / DISPLAY | FIELD TEST TERMINAL / DISPLAY | PREPARE FOR HOLD MODE / HOLD |
| DO NOTHING / THRESHOLD | DO NOTHING / THRESHOLD | PRE MEASURING / MEASURE | THRESHOLDING / THRESHOLD | DO NOTHING / DISPLAY | COMMAND FROM PC / DISPLAY | FIELD TEST TERMINAL / DISPLAY | DO NOTHING / THRESHOLD |
| DO NOTHING / MEASURE | DO NOTHING / MEASURE | POST MEASURING / MEASURE | MEASURING / MEASURE | REALIGN / MEASURE | COMMAND FROM PC / DISPLAY | FIELD TEST TERMINAL / DISPLAY | DO NOTHING / MEASURE |
| DO NOTHING / OPTIONS | DO NOTHING / OPTIONS | POST OPTIONS / DISPLAY | DO NOTHING / OPTIONS | DO NOTHING / OPTIONS | DO NOTHING / OPTIONS | DO NOTHING / OPTIONS | DO NOTHING / OPTIONS |
| DO NOTHING / HIDDEN | DO NOTHING / HIDDEN | POST HIDDEN / DISPLAY | DO NOTHING / HIDDEN | DO NOTHING / HIDDEN | DO NOTHING / HIDDEN | DO NOTHING / HIDDEN | DO NOTHING / HIDDEN |

AUTOMATED HAND-HELD KERATOMETER

This application is a continuation of U.S. patent application Ser. No. 07/775,194, filed Oct. 11, 1991, now U.S. Pat. No. 5,585,873.

I. BACKGROUND OF THE INVENTION

A. Field of the Invention

This invention relates to keratometers, and in particular, to an automated keratometer, including one that is relatively small in size, and hand-held.

B. Problems in the Art

1. Definition of Keratometer

A keratometer is an instrument utilized to measure the radius of curvature of a curved surface; generally that of an eye. Readings are usually taken of the radius of curvature of two different axes, as well as the angle of those two different axes. The results are utilized to estimate the dioptric power along each axis, which can then be used to estimate refractive power and/or shape of the particular eye being tested.

The primary readings taken by the keratometer are the curvature along the axis of maximum curvature, the curvature along the axis of minimum curvature, and the angles of the two curvature axes with respect to the horizontal axis. These types of readings are used to fit eye glasses or contact lenses. Accuracy is therefore important. This is particularly true for contact lenses which are placed in direct contact with the surface of the eye.

Keratometers are also used to examine the pathology of the cornea for such things as keratoconus, dystrophies, and stigmatism, corneal problems, and abnormal curvature. It is usually a standard piece of equipment for an optometric or ophthalmic examination.

2. Manual Keratometers

Keratometers originally were all manually operated optical devices. They continue to be used today. A manual keratometer requires the patient's head to be accurately positioned and maintained in position with respect to the device. Manual dials are then turned by the operator to create some optically perceivable condition in the device. Some manual keratometers require the operator to align several circles in a particular orientation while viewing the patient's eye. A reading is then taken from the dials or, in the earliest versions, a chart is consulted to obtain the readings. These readings must then be manually transcribed.

Manual keratometers represent a substantial investment, and require substantial space in an office for the patient and operator to complete the procedure. Perhaps the most significant problems of manual keratometers are the amount of time required to take the appropriate readings and the amount of training and expertise needed by the operator to achieve reliable results.

Operation of these devices requires some level of advanced skills and knowledge. They generally must be operated by ophthalmologists, optometrists, or perhaps opticians. Some judgment and experience on a rather high level is needed to take and interpret the readings and create the conditions needed to ensure the readings will be generally accurate and reliable.

Manual operation includes potential for human error. The operator must take significant care in the procedures and may need to retake the measurements to double check original measurements. Sometimes interpretation of results is needed, requiring substantial expertise.

Manual keratometers generally allow apical measurements only, and do not allow peripheral cornea measurements. New surgeries and treatment techniques require accurate peripheral measurements. Manual keratometers also have a number of moving parts and rely on expensive high precision optical elements. Calibration and the maintenance of calibration is therefore very important. All of the above discussed problems leave room for improvement in this field.

3. Automated Keratometers

In an attempt to meet these needs, automated keratometers have been developed. These devices generally utilize some electro-optical combination to provide keratometric readings which can be displayed, stored, or sometimes printed. Major deficiencies of present automated systems are as follows.

Many of these devices require a substantial amount of manual operation. Some require that the operator align the instrument to the eye by viewing and aligning images in the keratometer optical system. One requires alignment of lights and geometric figures. This requires the operator to subjectively determine whether a certain somewhat subjective condition exists, introducing an element of error risk.

These systems require the user's head to be fixed with respect to the machine. Normally this will include a chin or head brace and necessitates constant vigilance to ensure that the head is kept in a fixed position.

Most automated keratometers take up a substantial amount of space. Many consume the better part of a medium sized table. The operator sits on one side of the machine, while the patient sits on the other. It might also require associated equipment, taking even more room.

It is to be understood that the size of some automatic keratometers is so large that it must be put in a separate room, or at least a room outside of the normal examination room. This requires additional patient shuffling from the waiting area to the examination room, to the room for the keratometric readings, and so on. This further complicates and is an obstacle to efficiency of patient processing. It can create a bottle neck if all the patients need to go to a separate room, have keratometric readings taken, and then return to the examination room.

Auxiliary equipment such as motorized tables and chairs is sometimes utilized with the automated keratometer to accurately position the patient. This adds significantly to the cost and to the space needed for operation. These machines tend to be heavy and their inner contents somewhat fragile. Most also require precise optical components. They are also extremely costly as compared with manual keratometers.

Automated keratometers therefore include potential errors associated with the requirement of human verification or subjective determinations. They also rely on precise, costly optical components which must be maintained in precise alignment and calibration.

They also require a high level of operator training and expertise. The added cost and space required for these devices may therefore offset any improvement they provide in time or accuracy.

4. Size and Space Considerations

Keratometers are generally utilized in the offices of ophthalmologists and optometrists. They may also be utilized by opticians. Keratometric measurements are often taken for each patient's visit. This is especially true for those who wear contacts. The keratometer measures the curvature of the eye. The contact, to be fitted properly, is placed directly adjacent to the eye. Most ophthalmologists and optometrists set up "lanes" in each examination room. Patients are called from the waiting room and moved through a series of equipments or stations in the lane during eye examinations.

Much consideration is given into maximation of patient flow or turnover. Several patient rooms with completely furnished lanes are therefore utilized. While one patient is put through the measurements in the lanes, another patient can be brought into another room and prepared. A third patient who has finished with measurements can then be readied for completion of the exam while the ophthalmologist or optometrist goes to another room and/or another patient.

Time and space are primary factors in improving the efficiency of patient flow. More time to perform the keratometric measurements, translates into less time available to do other things. More room for the keratometer, translates into less room for other equipment, or a reduced number of patient rooms; which translates into more square footage and more costly office space. Less costly and smaller manual keratometers, are more time consuming to operate. Automated keratometers, take up much more room and are more cumbersome.

With current keratometers it is not possible to delegate the taking of keratometric readings to staff members. They require either substantial training and/or substantial expertise, knowledge, and skill to operate. These traits may not be readily available in staff members. At a minimum, there is a requirement of extensive or long training and experience. Otherwise accuracy and reliability may suffer substantially.

While automated keratometers are generally much more costly than manual keratometers, the trend is to purchase and use automated keratometers. There is a perception, perhaps primarily by patients, that automated, higher technology equipment is a necessity for competent and successful ophthalmological and optometrist practice.

5. Needs in the Art

Although automated keratometers are available, their problems and deficiencies are readily apparent as discussed above. A need therefore exists for an automated keratometer which is small in size, takes all keratometric readings quickly, accurately and reliably, and is easy for staff workers or technicians to operate.

There is also a need for a portable automated keratometer that need not be placed on a table nor require constraint of the patient's head. There is also a need for an automated keratometer which is less costly than current automated keratometers.

6. Objects

It is therefore a principal object of the present invention to provide an automated keratometer which solves the problems or improves over the deficiencies in the art.

Another object of the present invention is to provide an automated keratometer which is substantially automatic and eliminates substantially the margin of human error in its operation.

A still further object of the present invention is to provide an automated keratometer which can be hand held, is easily maneuverable, light weight, and can even be battery. powered.

A still further object of the present invention is to provide an automated keratometer which does not require fixed positioning of the patient's head or eye with respect to the device.

Another object of the present invention is to provide an automated keratometer which has an automated alignment system to ensure alignment during measurement.

Another object of the present invention is to provide an automated keratometer which helps patients fix on a target to eliminate possible measurement errors caused of loss of fixation or movement of the eye.

Another object of the present invention is to provide an automated keratometer which automatically processes, displays, and stores or prints keratometric readings.

Another object of the present invention is to provide an automated keratometer which allows the user to simultaneously view the patient's eye.

These and other objects, features, and advantages of the present invention will become more apparent with reference to the accompanying specification and claims.

II. SUMMARY OF THE INVENTION

The invention is an automated keratometer which is portable and hand held. It is freely and easily movable into a position near a patient's eye and does not require the patient to have his/her head fixedly secured.

A portable housing contains a projector system and a camera system. The projector system includes a plurality of collimated light sources which project out of the housing onto the patient's eye. The housing is moved to a position where the projected light sources circumferentially surround the optical axis of the eye. The position of the housing is also adjusted so that the optical axis of the eye is made generally co-linear with an optical axis through the keratometer through the camera means. The camera means is positioned telecentrically along the optical axis. It captures the reflected image of the projected light sources on the eye. A processing means then determines the relative spatial locations of the reflected light sources and derives radii of curvature measurements according to an algorithm in the processing means.

The invention includes optional features and enhancements such as alignment means for automatically indicating alignment along the optical axis. A fixation means is also provided to assist the patient in fixing his/her eye during measurement. A leveling means can also be incorporated to automatically indicate the housing is in a level position.

The keratometer can be battery powered and optionally can be rechargeable. It can include a display so that the calculated keratometric measurements can be observed by the operator. It can also store those measurements to be printed out or otherwise documented.

The invention therefore will completely free the operator and patient of the requirement of dealing with a table top device taking up substantial space, and will take quick and accurate readings. Its level of automation reduces potential for error and its combination of components reduces the cost to manufacture, assemble, and therefore retail the device.

III. BRIEF DESCRIPTION OF THE DRAWINGS

FIG. 1 is a perspective view of a preferred embodiment of the invention.

FIG. 2 is a slightly enlarged side elevational and partial sectional view of FIG. 1.

FIG. 7 is a still further enlarged sectional view taken along line 7—7 of FIG. 6.

FIG. 8 is still a further enlarged sectional view taken generally along line 8—8 of FIG. 7.

FIG. 9 is an isolated partial sectional side elevational view of the optic system of the preferred embodiment of the present invention.

Figure 13A:
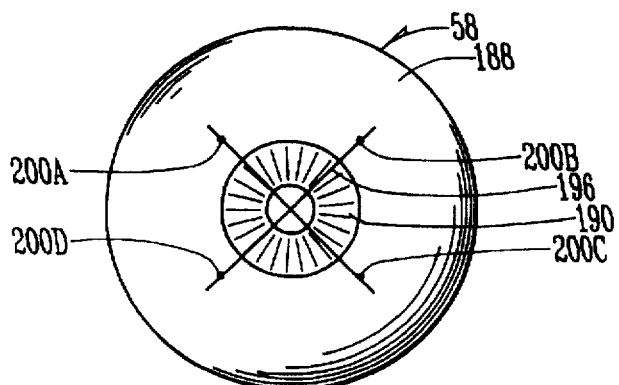
Figure 13B:
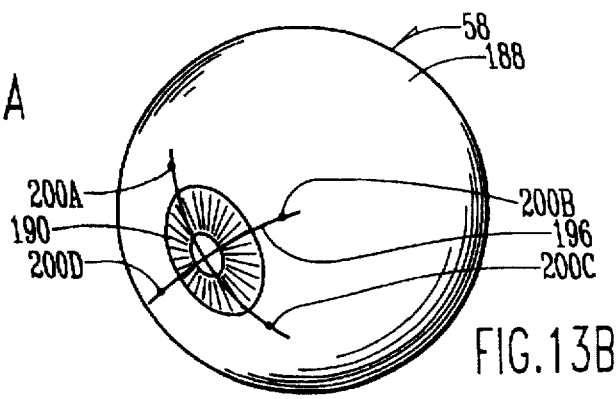
Figure 13C:
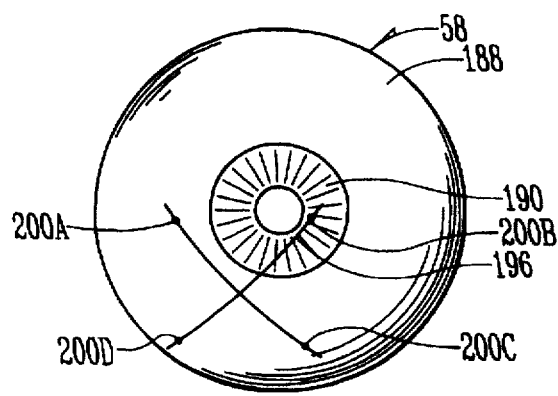
Figure 13D:
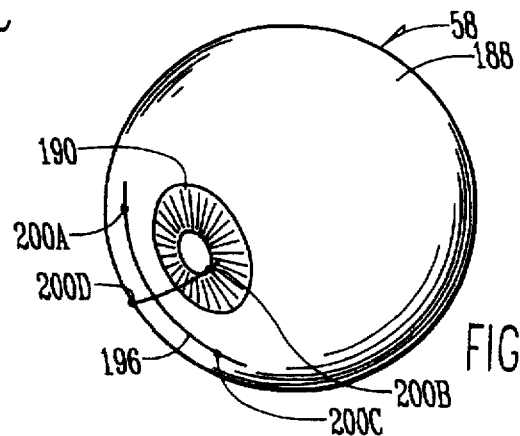

FIGS. 13A-D are diagrammatical depictions of an eye and keratometric measurements generally taken with a keratometer. FIGS. 13A and 13B depict radii of curvature measures centered on the cornea. FIGS. 13C and 13D depict the same but centered off the cornea.

FIGS. 14A-G are diagrammatical representations of various status conditions during operation of the keratometer as viewed through the eye piece of the preferred embodiment of the keratometer.

FIG. 15 is a diagrammatic representations of FIG. 14G as captured by a camera means according to the preferred embodiment of the present invention.

Figure 16A:
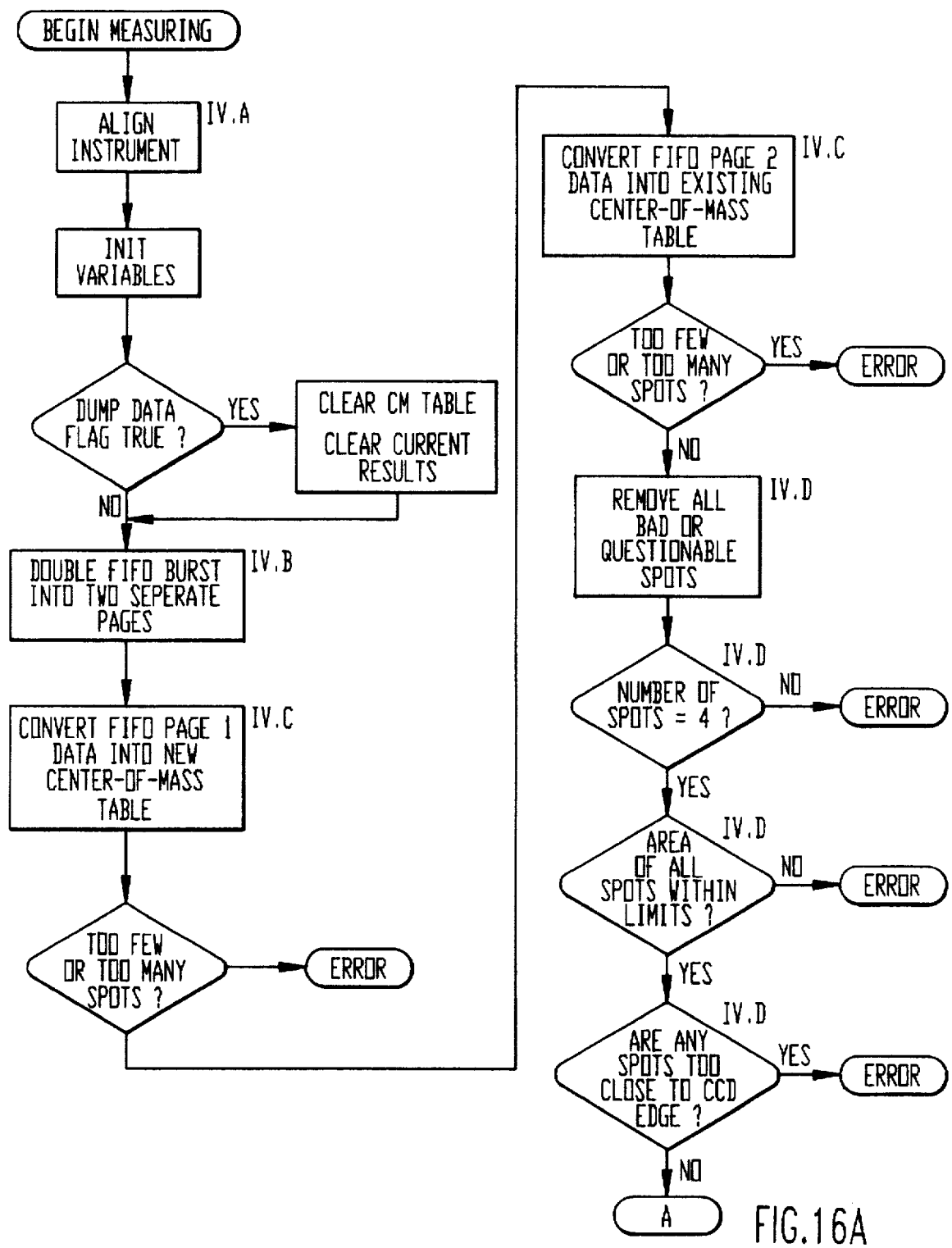
Figure 16B:
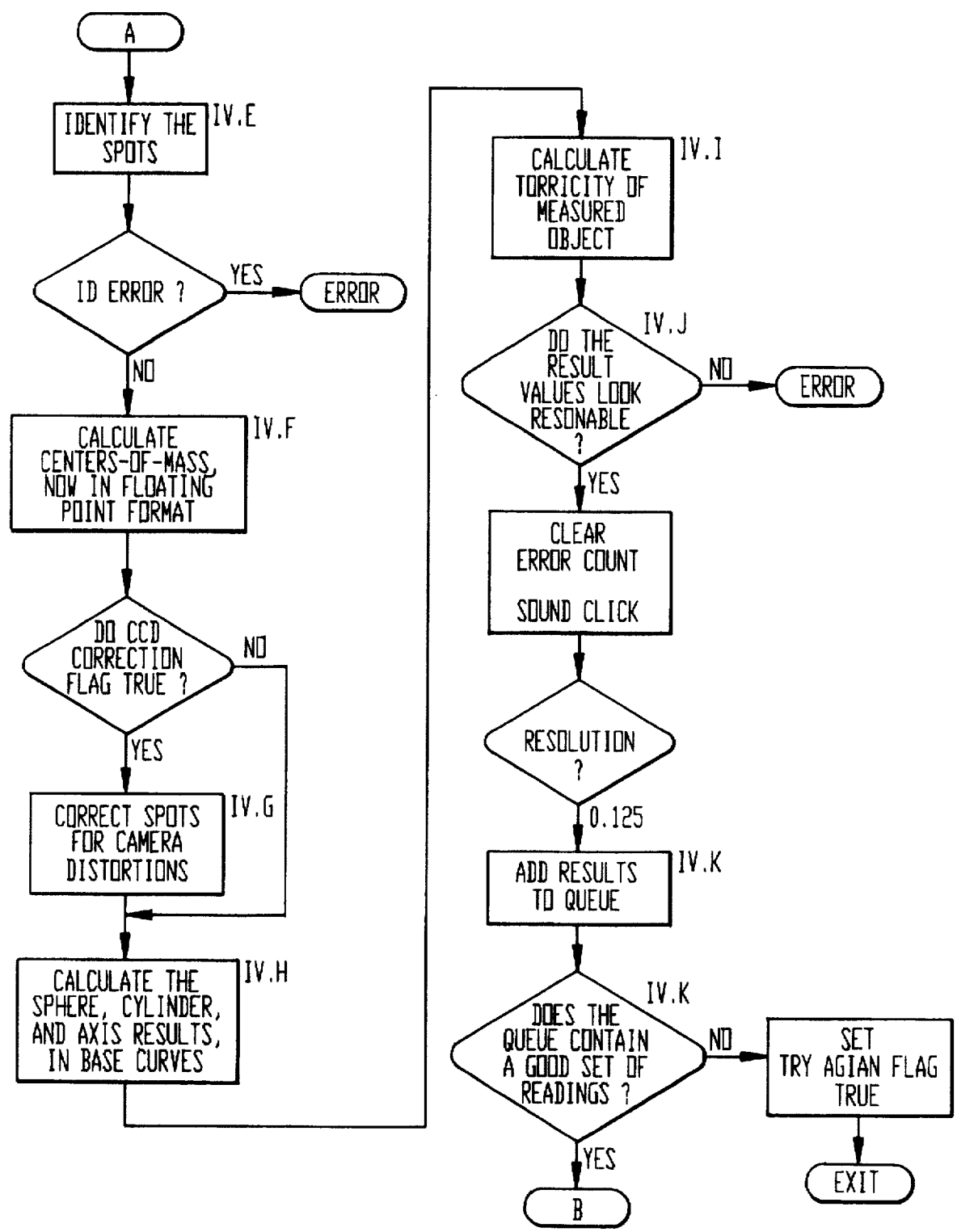
Figure 16C:
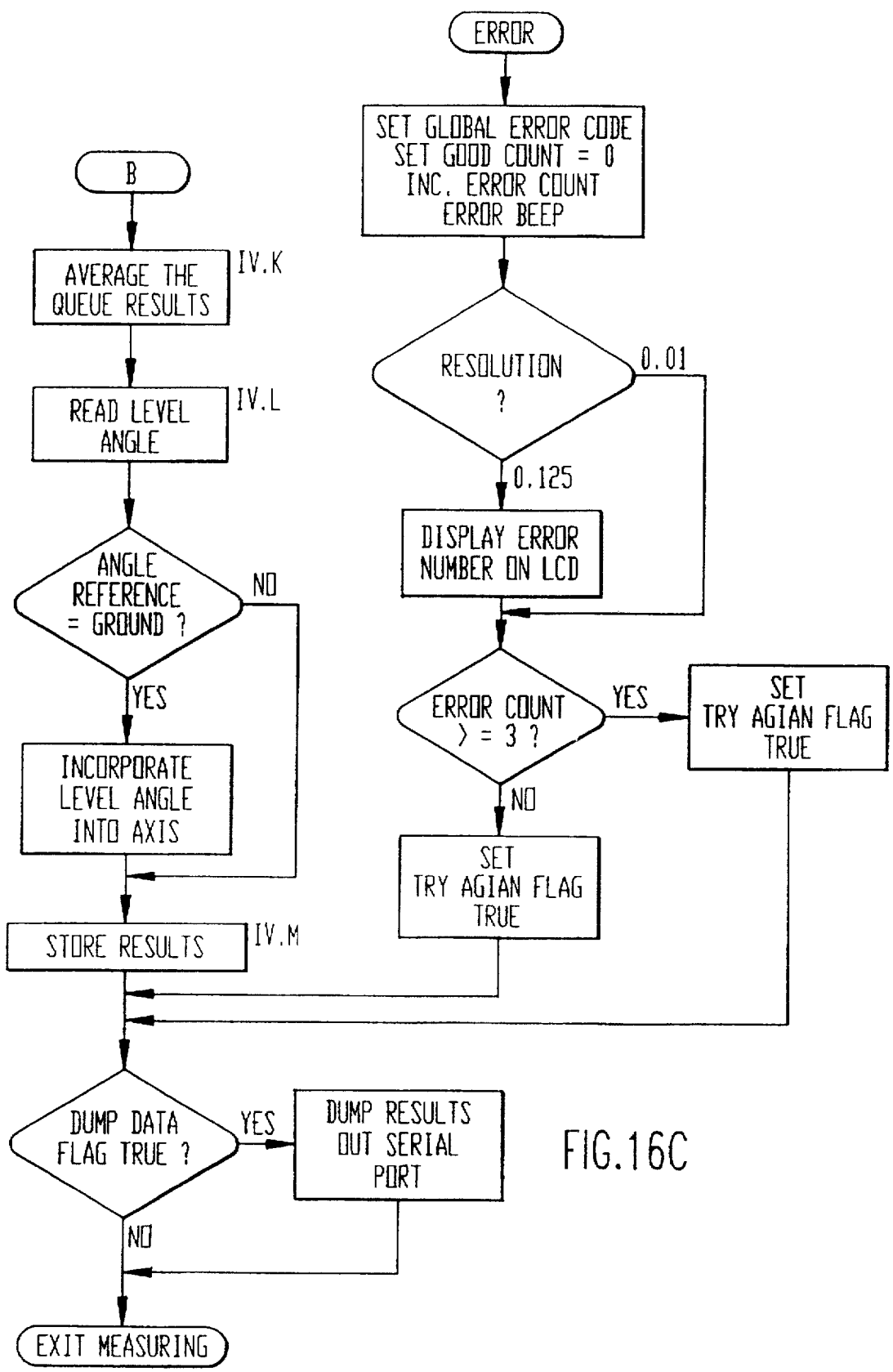

FIGS. 16A-16C are diagrammatic depictions of a flow chart of software operation of the preferred embodiment of the present invention.

FIG. 17 is the general block diagram of the electrical circuitry of the preferred embodiment of the present invention.

Figure 18:
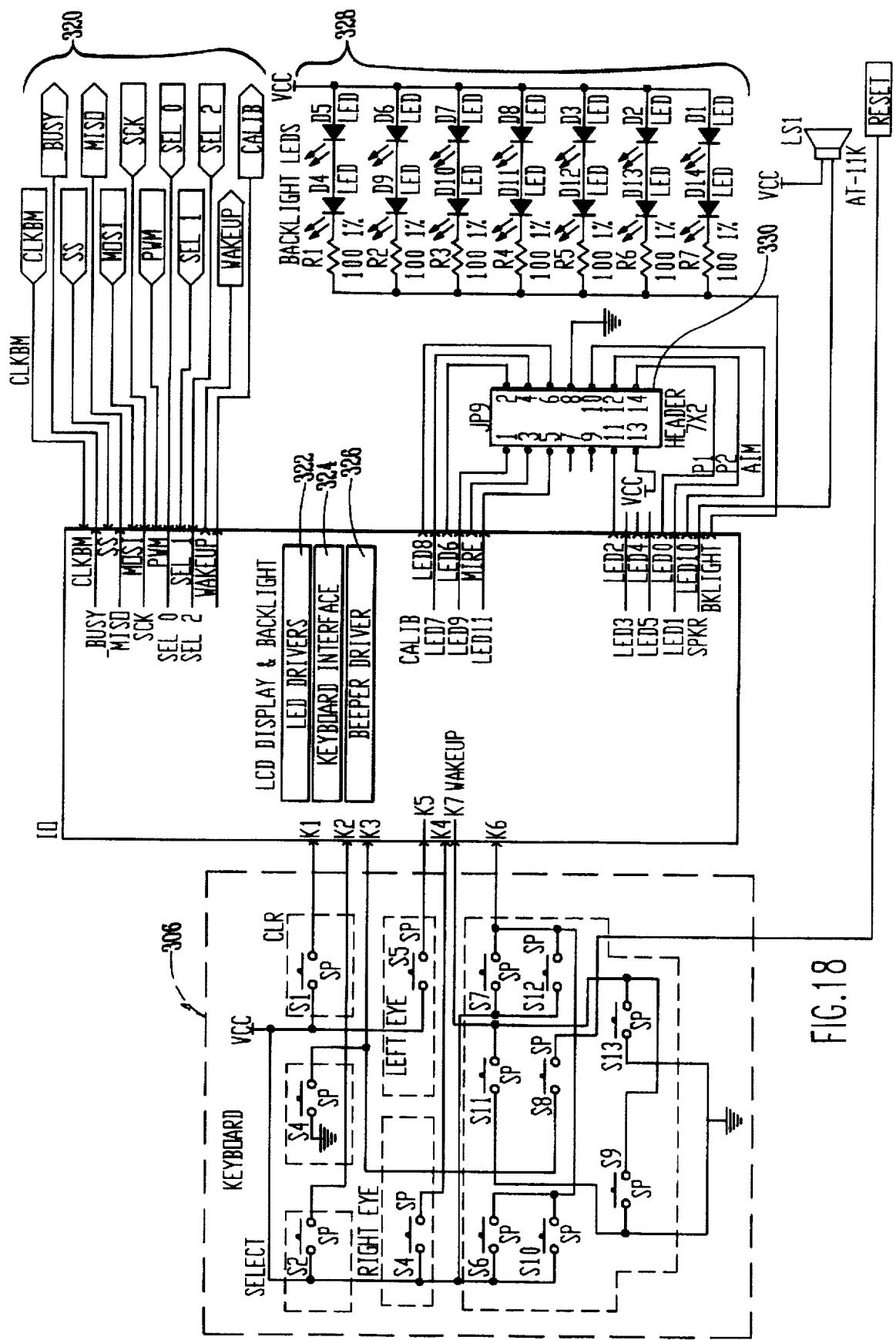

FIG. 18 is a more detailed partial schematic partial block diagram of the input/output section of FIG. 17.

Figure 19A:
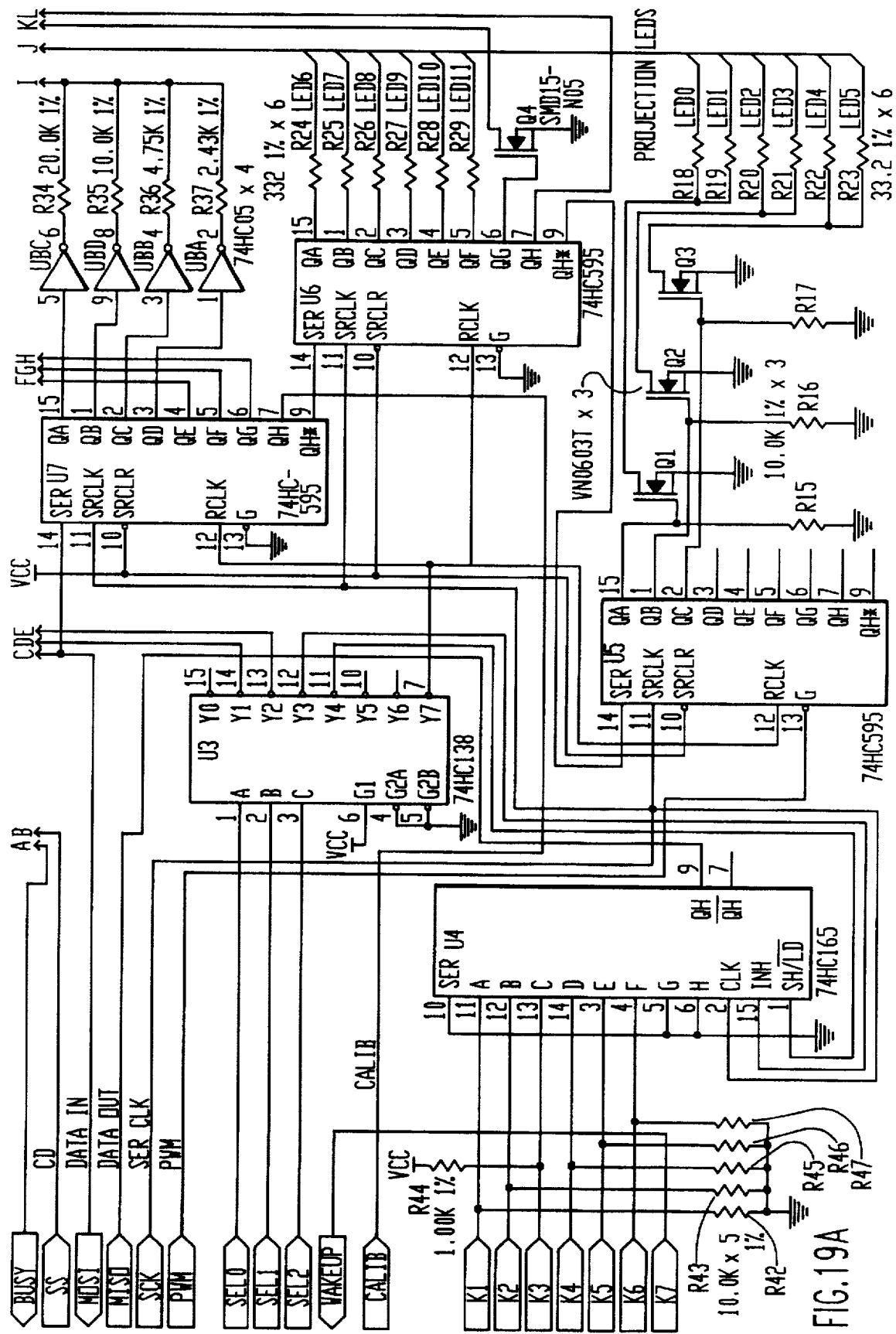
Figure 19B:
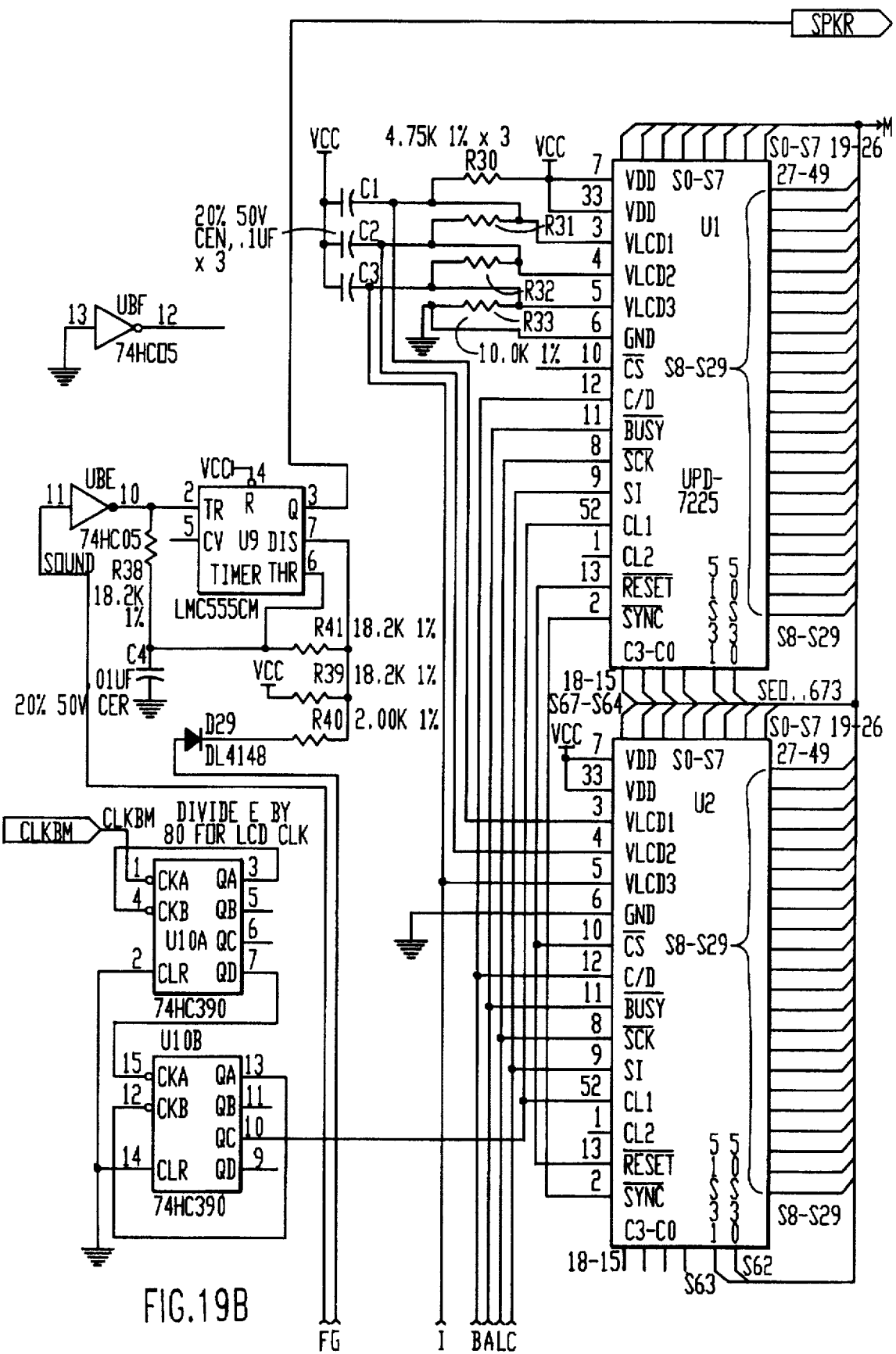
Figure 19C:
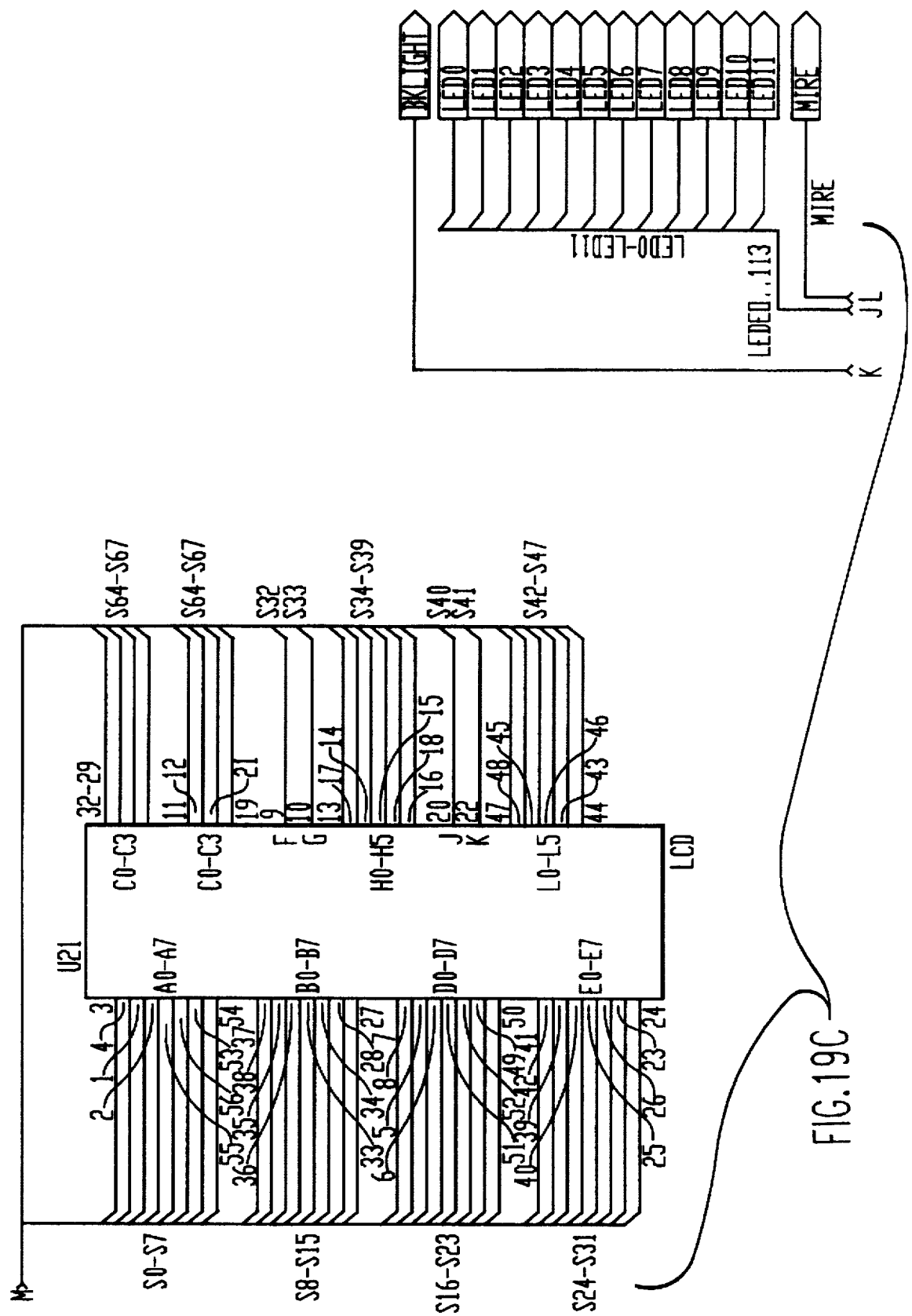

FIG. 19A-19C is a detailed electrical schematic of the input/output section of FIG. 18.

Figure 20:
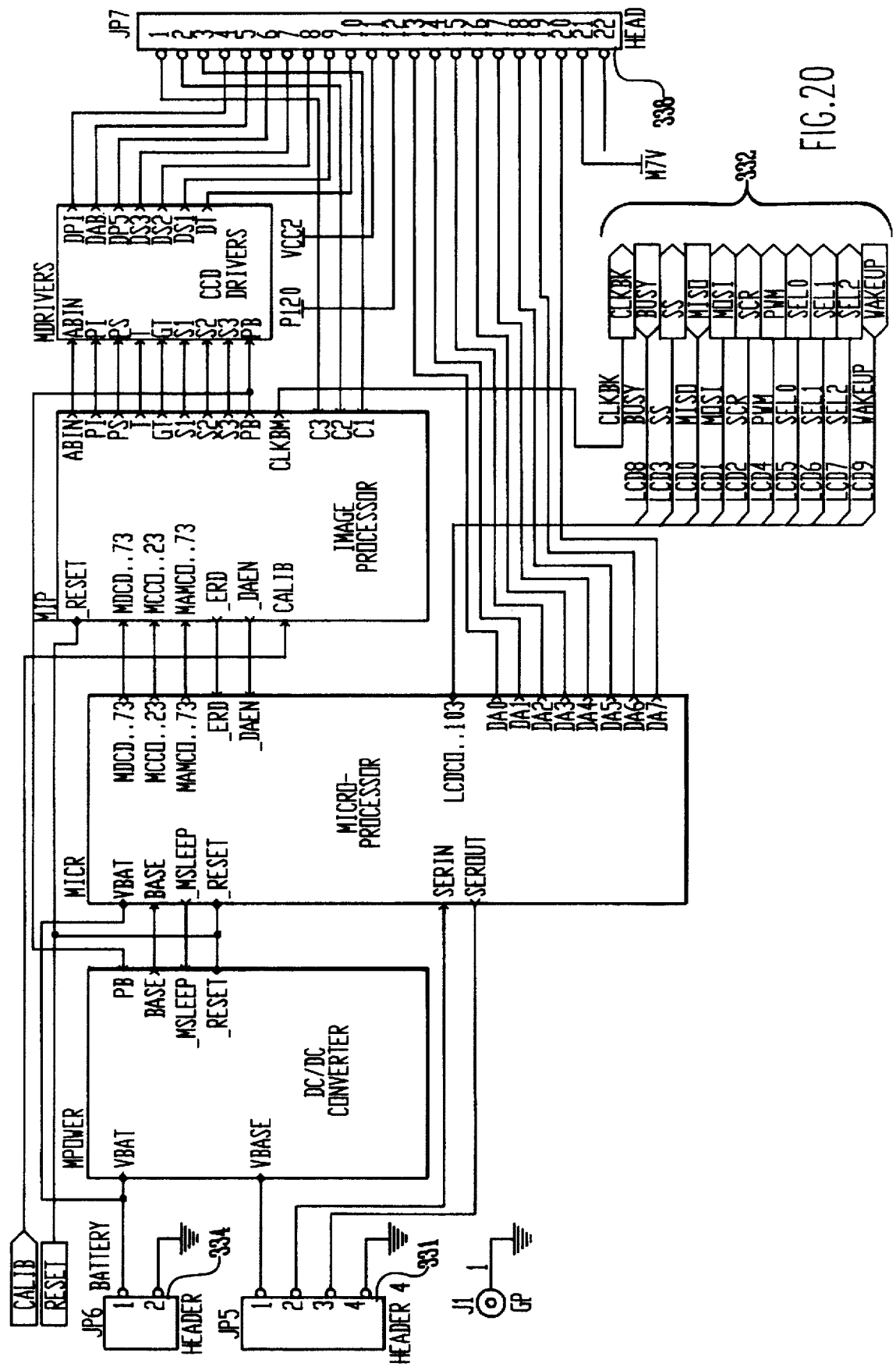

FIG. 20 is a partial schematic, partial block diagram of the main board of FIG. 17.

Figure 21:
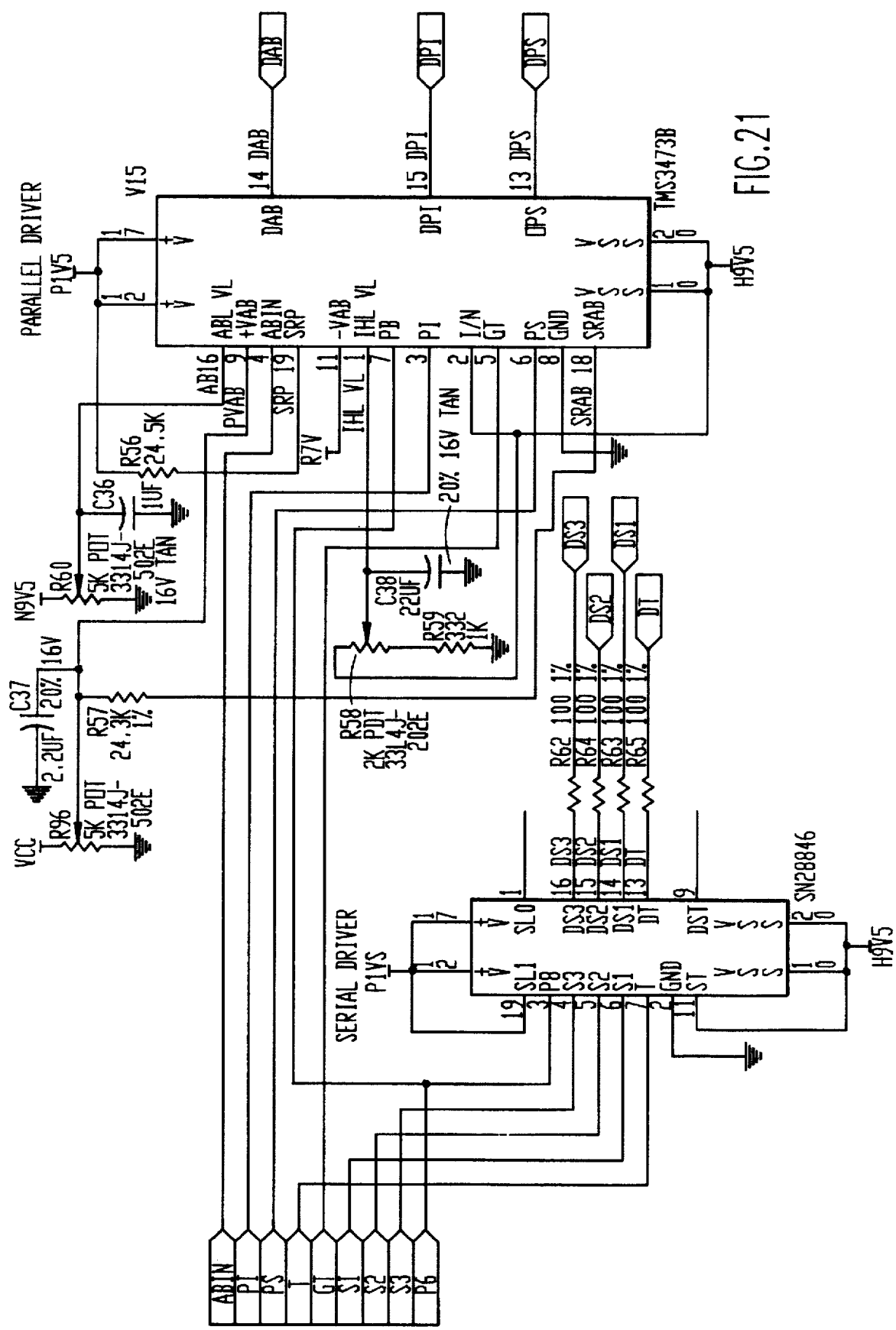

FIG. 21 is a detailed electrical schematic of the CCD driver section of FIG. 20.

Figure 22:
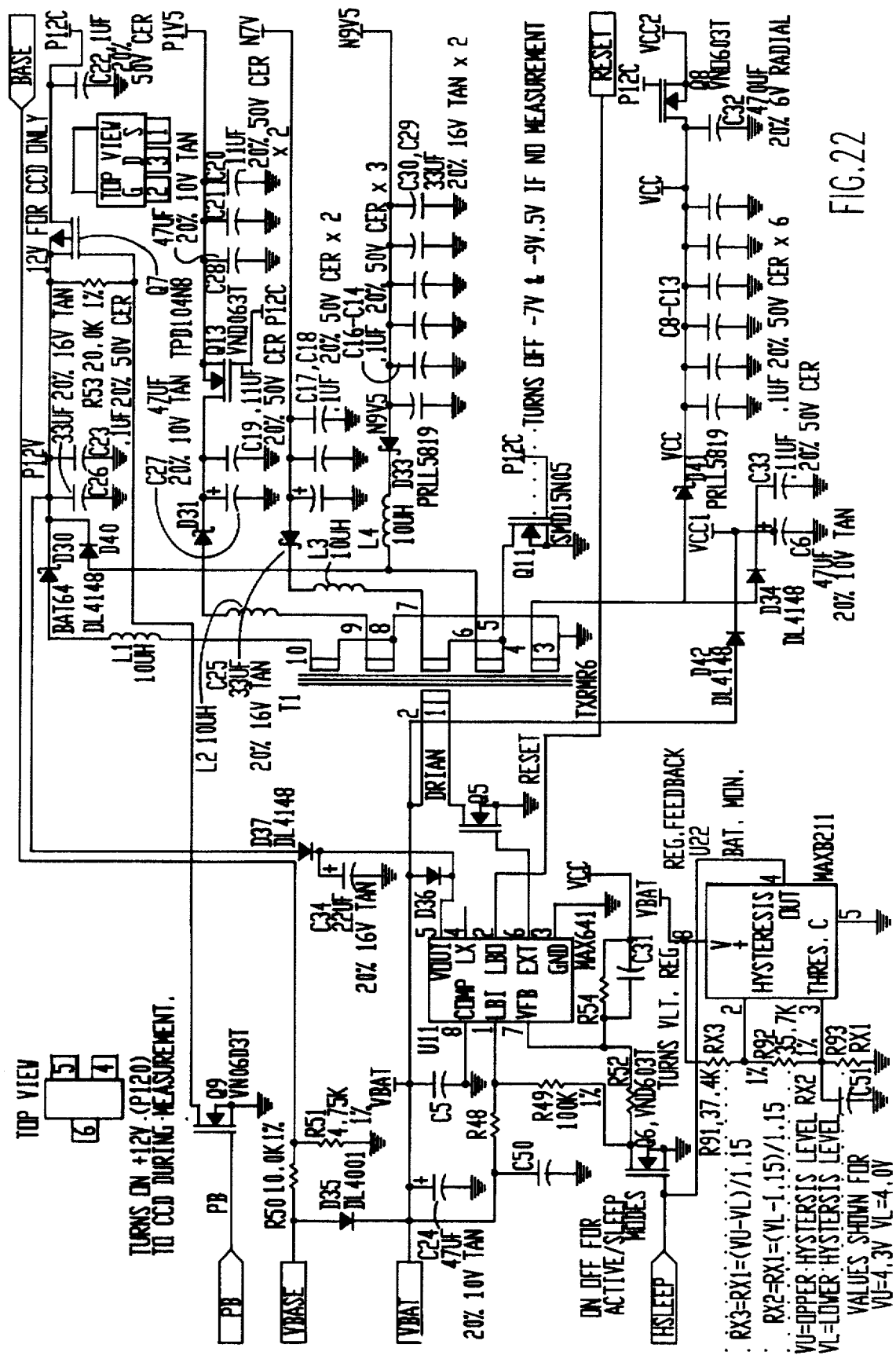

FIG. 22 is a detailed electrical schematic of the power supply circuit of the preferred embodiment of the present invention.

Figure 23:
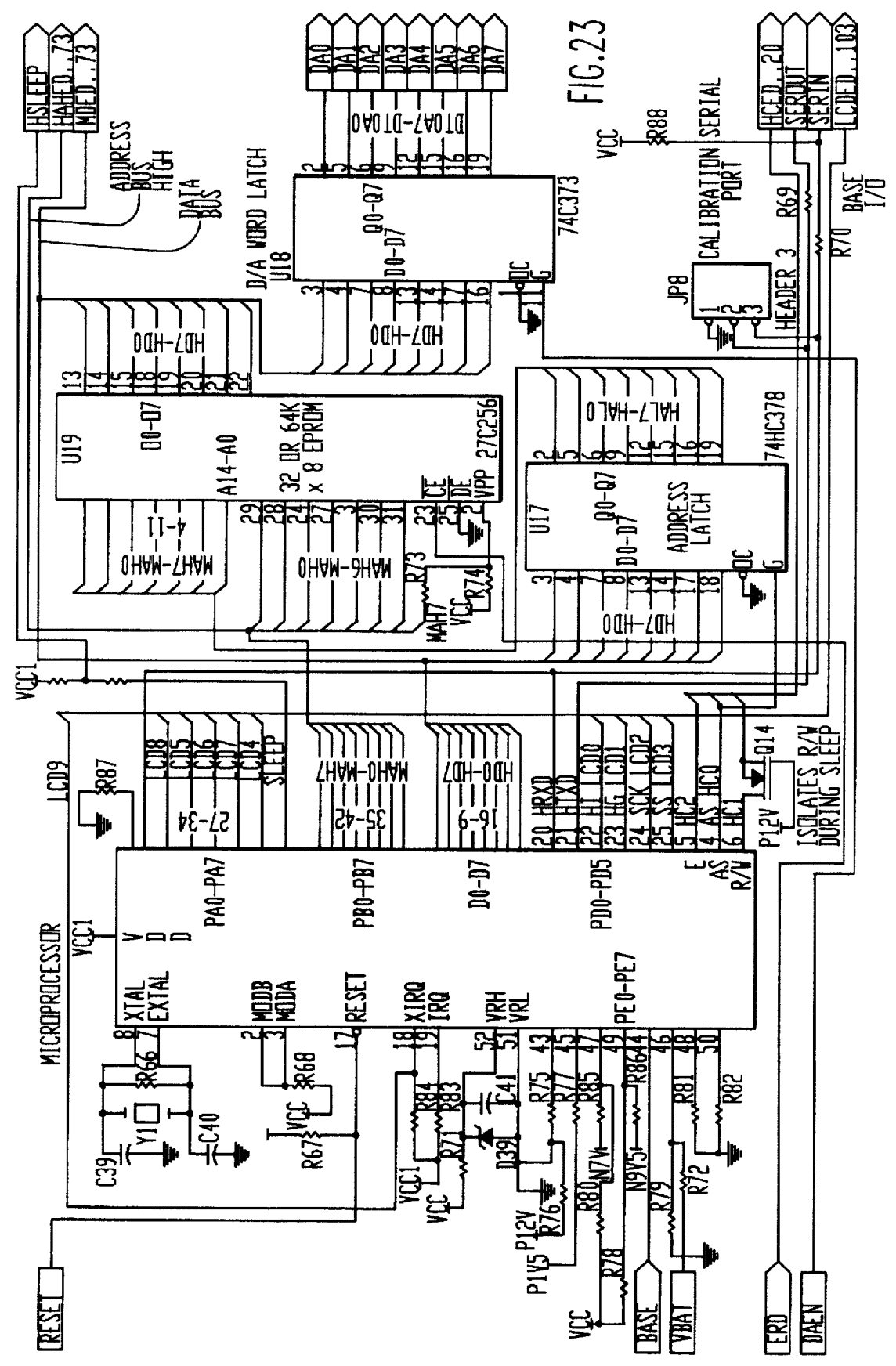

FIG. 23 is a detailed electrical schematic of the microprocessor of FIG. 20.

Figure 24:
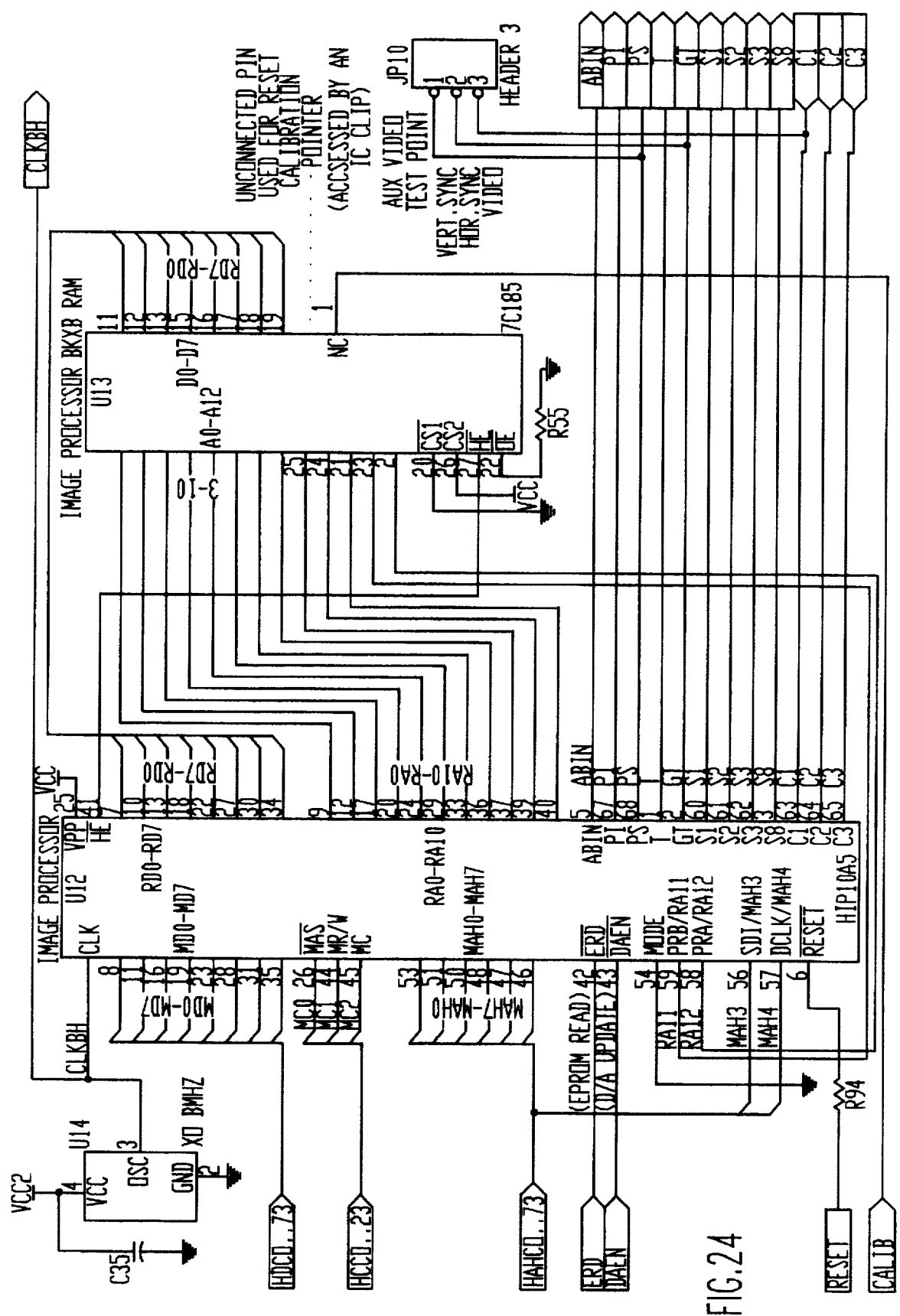

FIG. 24 is a detailed electrical schematic of the image processor of FIG. 20.

Figure 25:
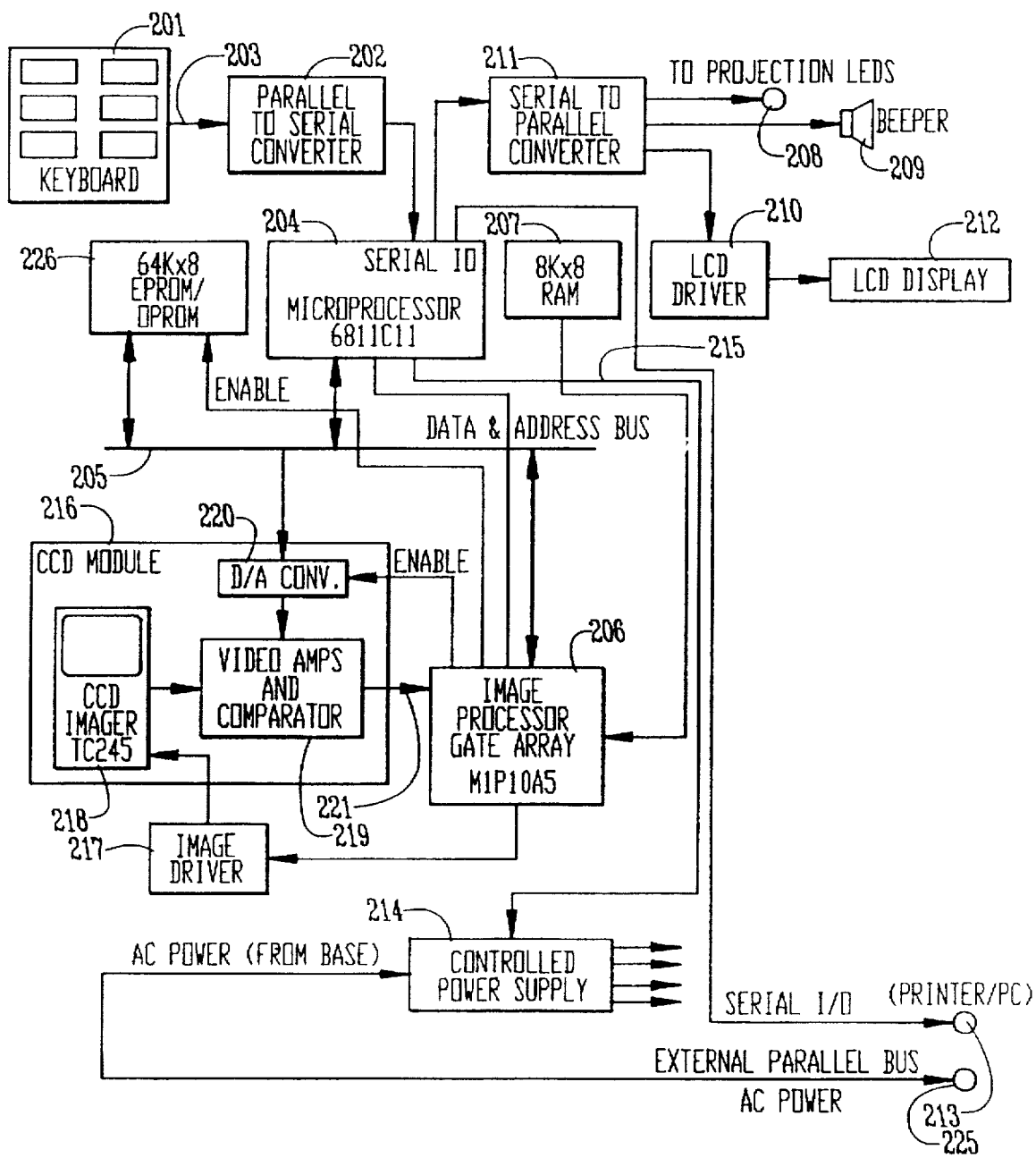

FIG. 25 is a block diagram of the overall circuit for the preferred embodiment of the invention.

Figure 26:
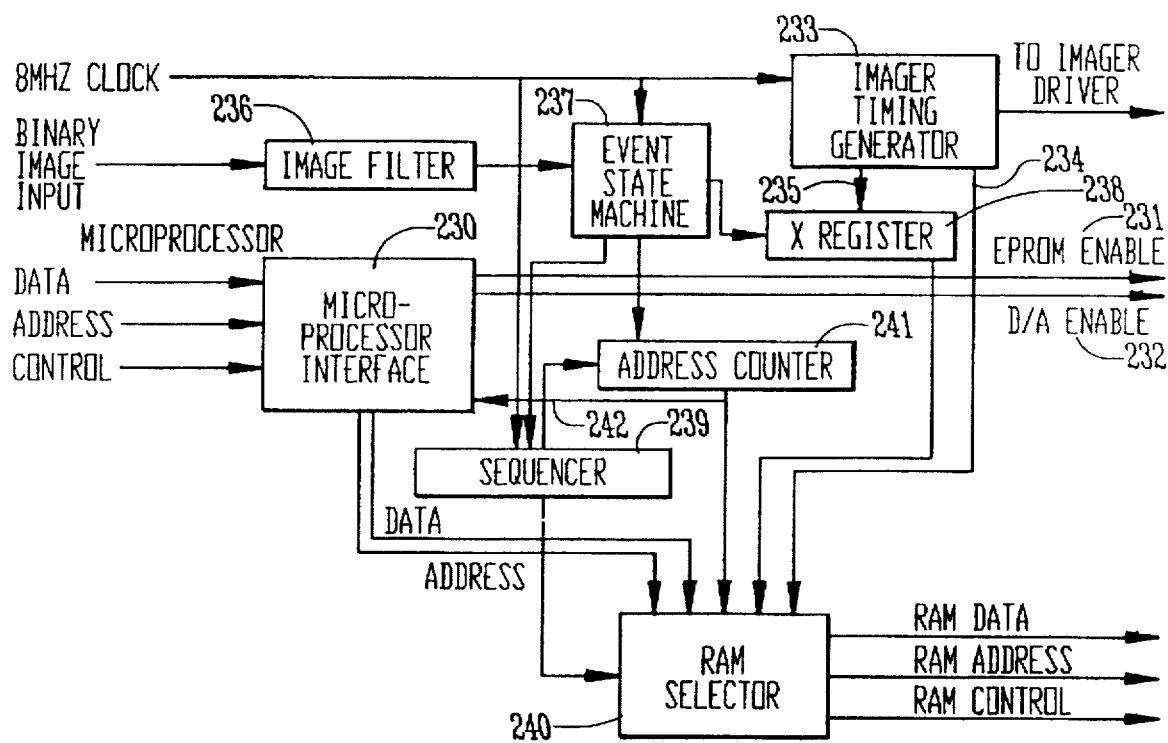

FIG. 26 is a block diagram of the image processor gate array of FIG. 25.

Figure 27:
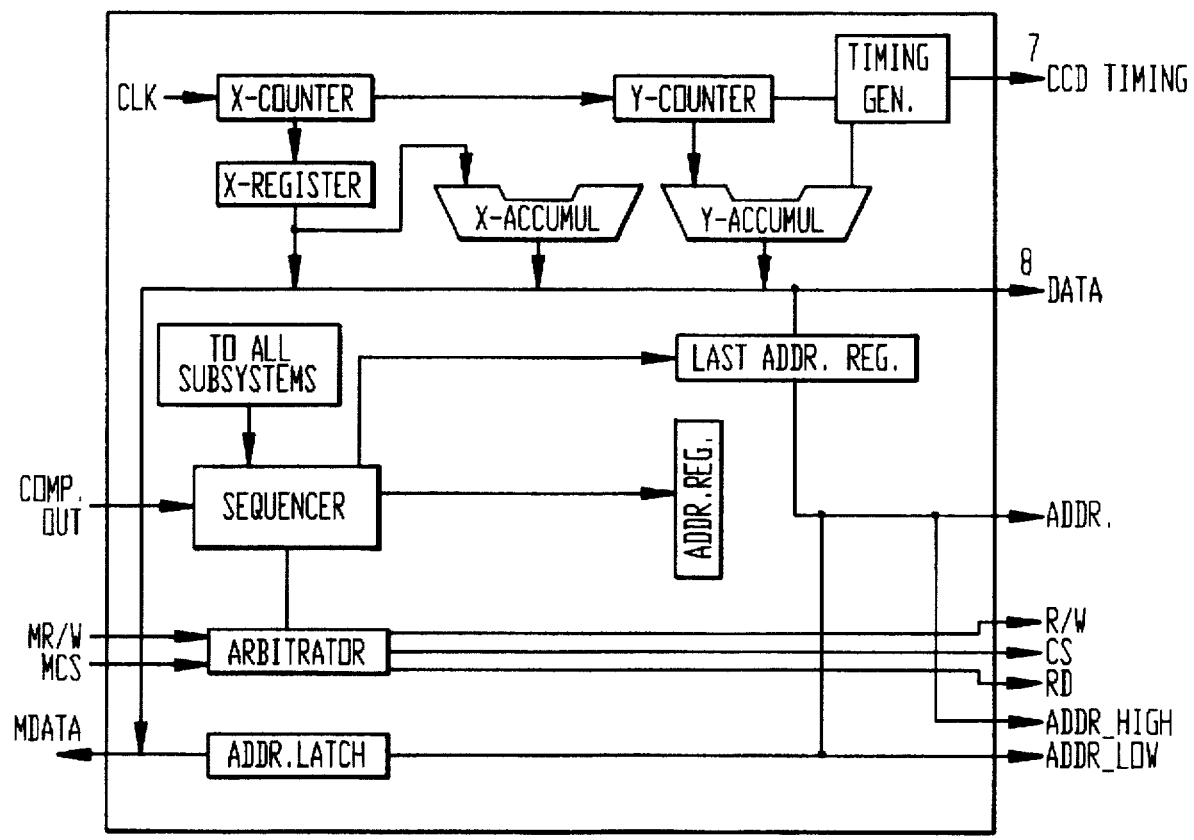

FIG. 27 is an internal block diagram for the gate array.

Figure 28:
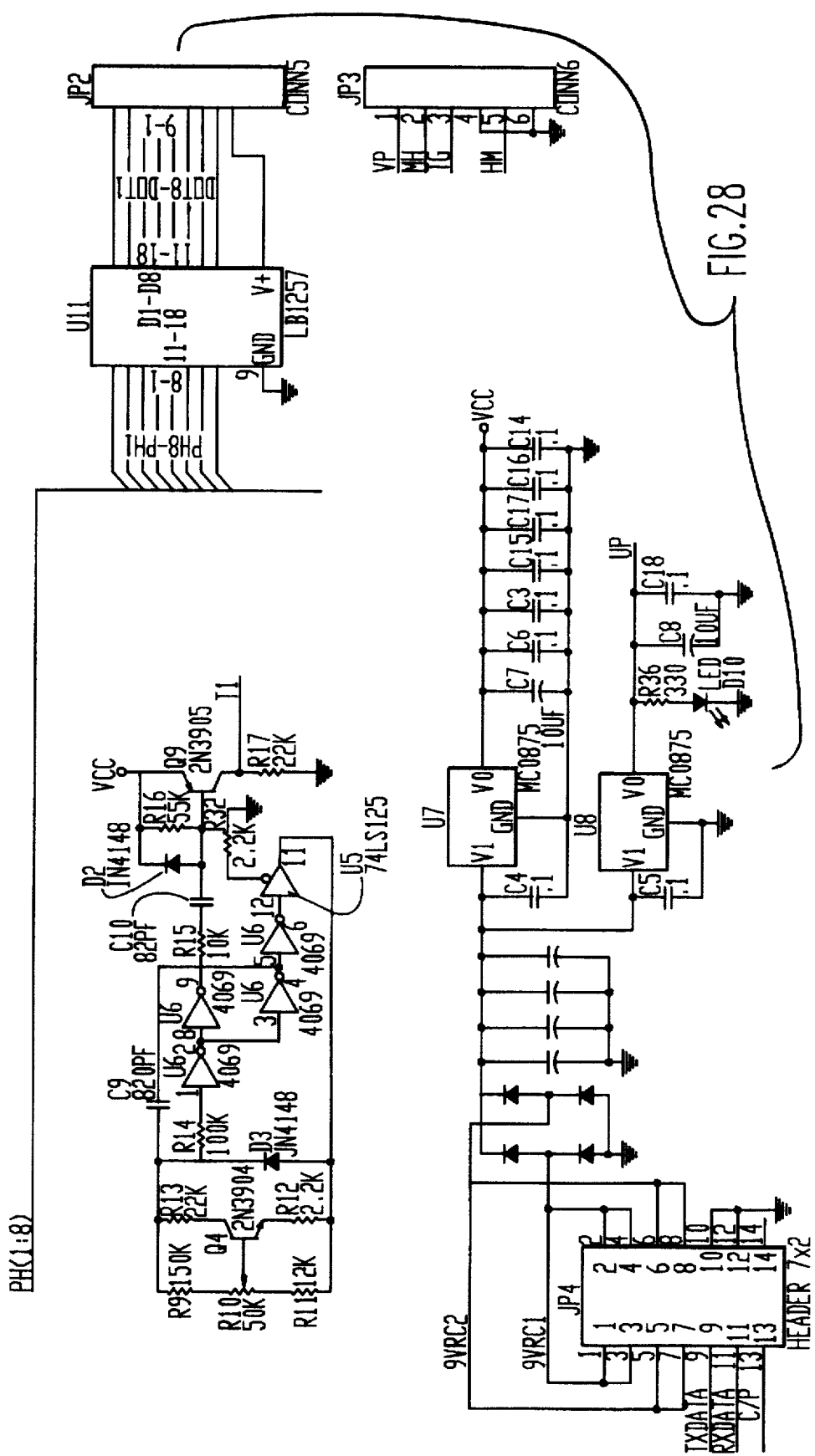
Figure 29:
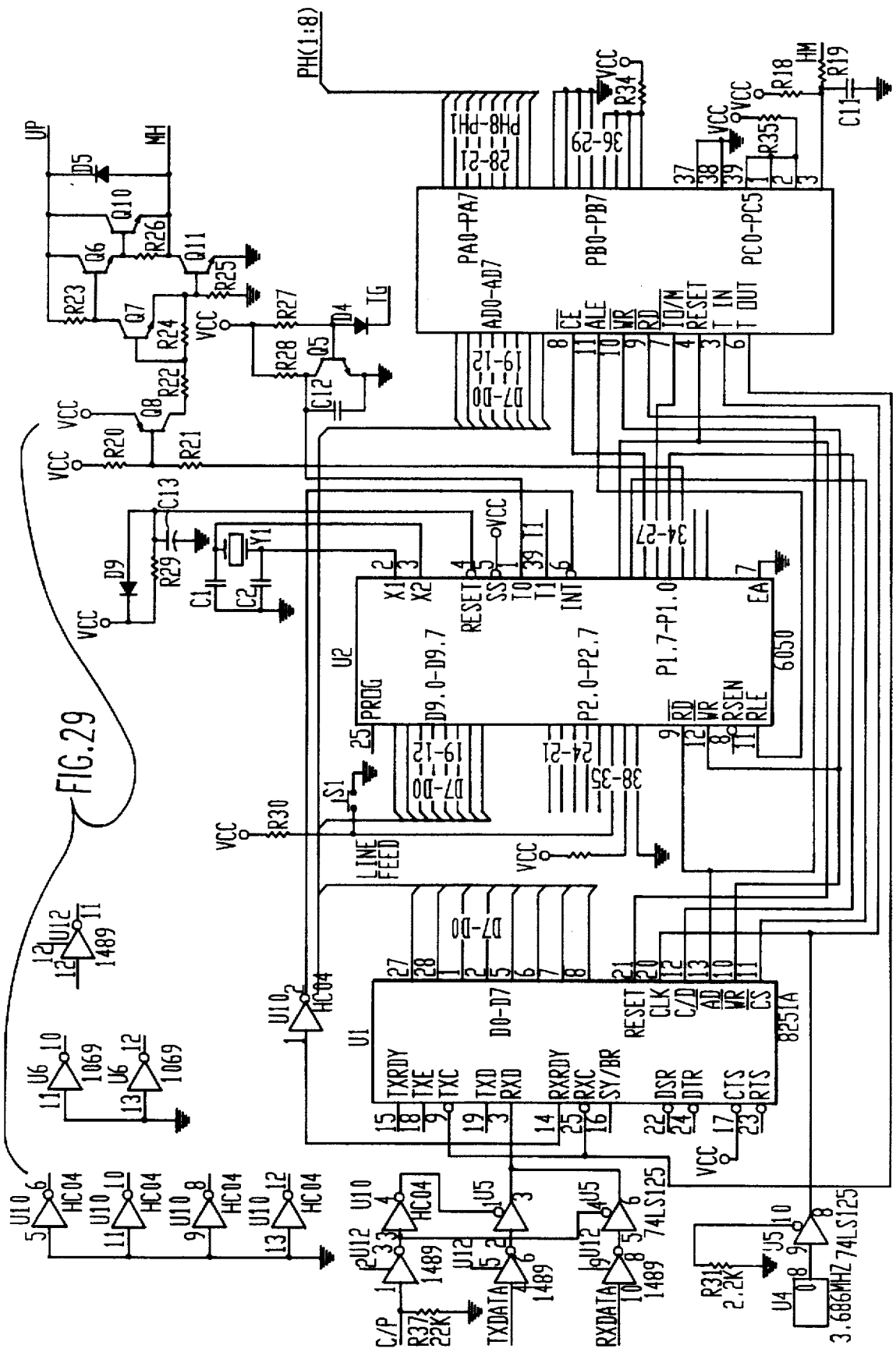

FIGS. 28-29 are electrical schematics for a printer driver that can be used with the preferred embodiment of the invention.

Figure 30:
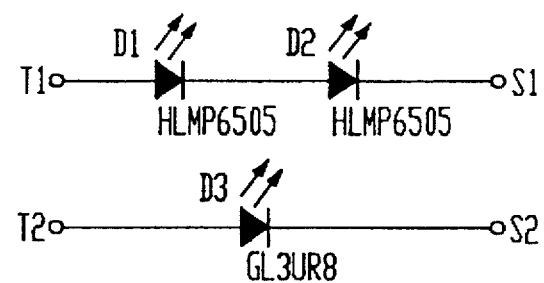

FIG. 30 is an electrical schematic of a projector printed circuit board that can be used with the preferred embodiment of the invention.

Figure 31:
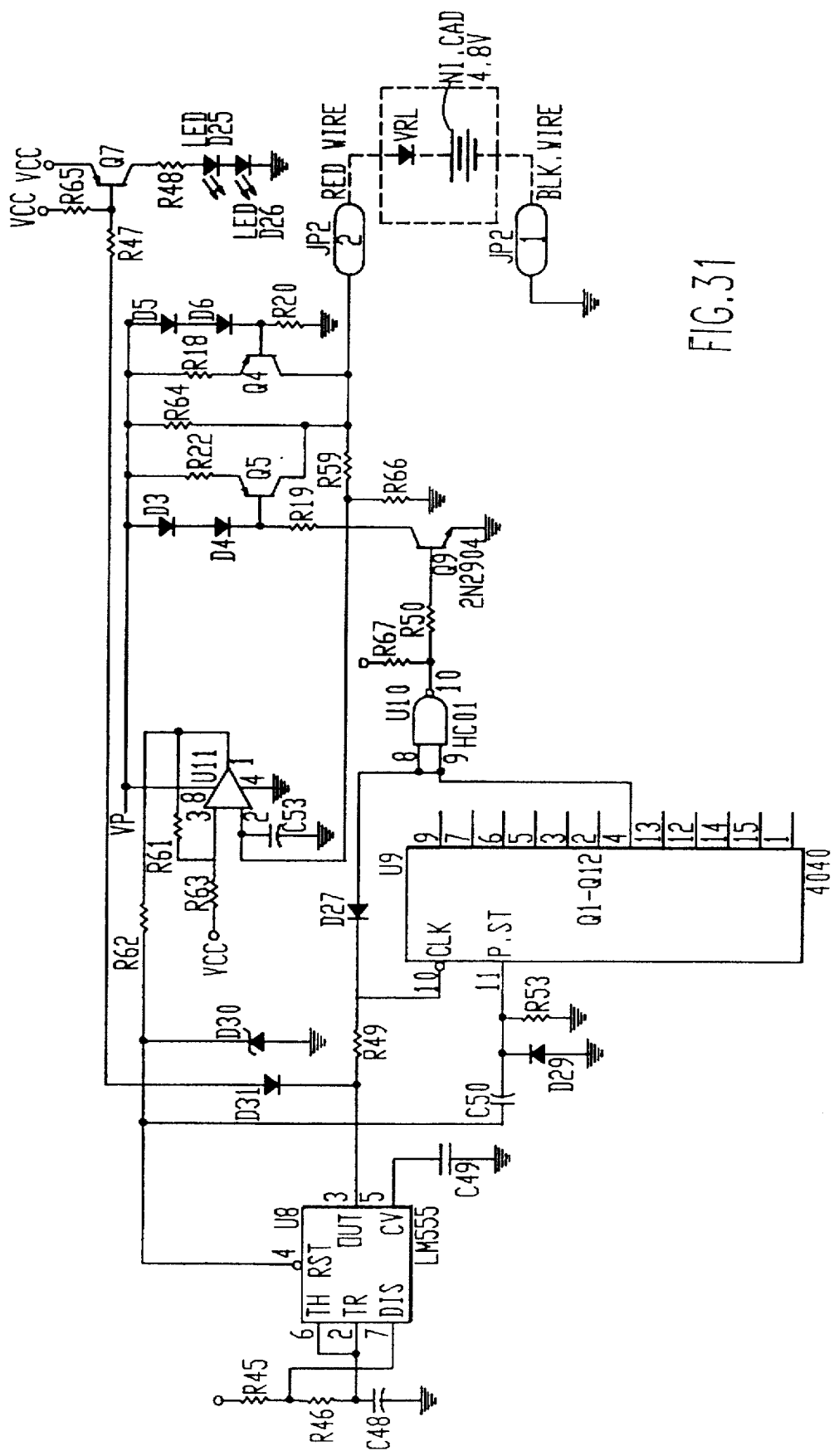
Figure 32:
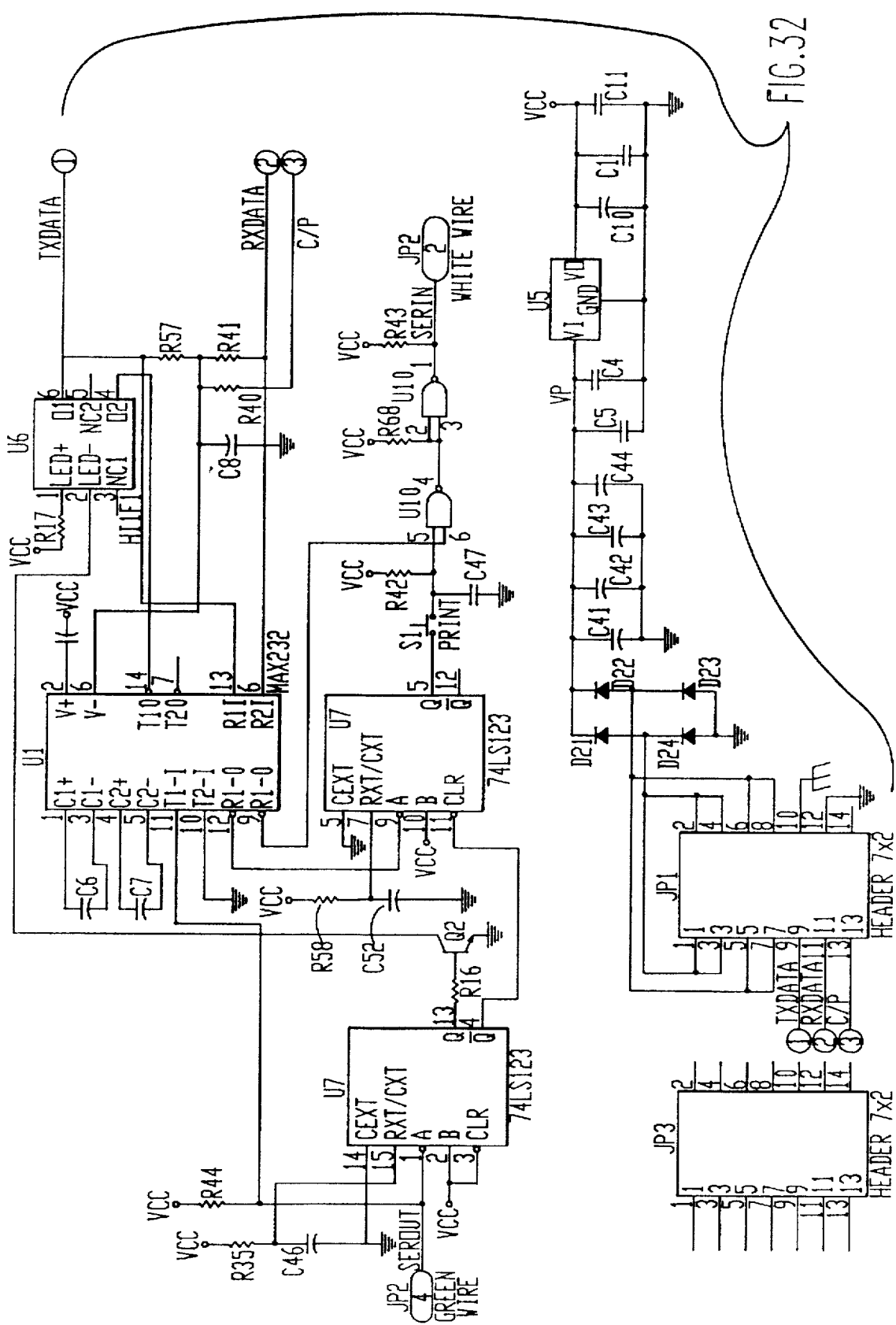

FIGS. 31-32 are electrical schematics for circuitry that can be used with the base of the preferred embodiment of the invention.

Figure 33:
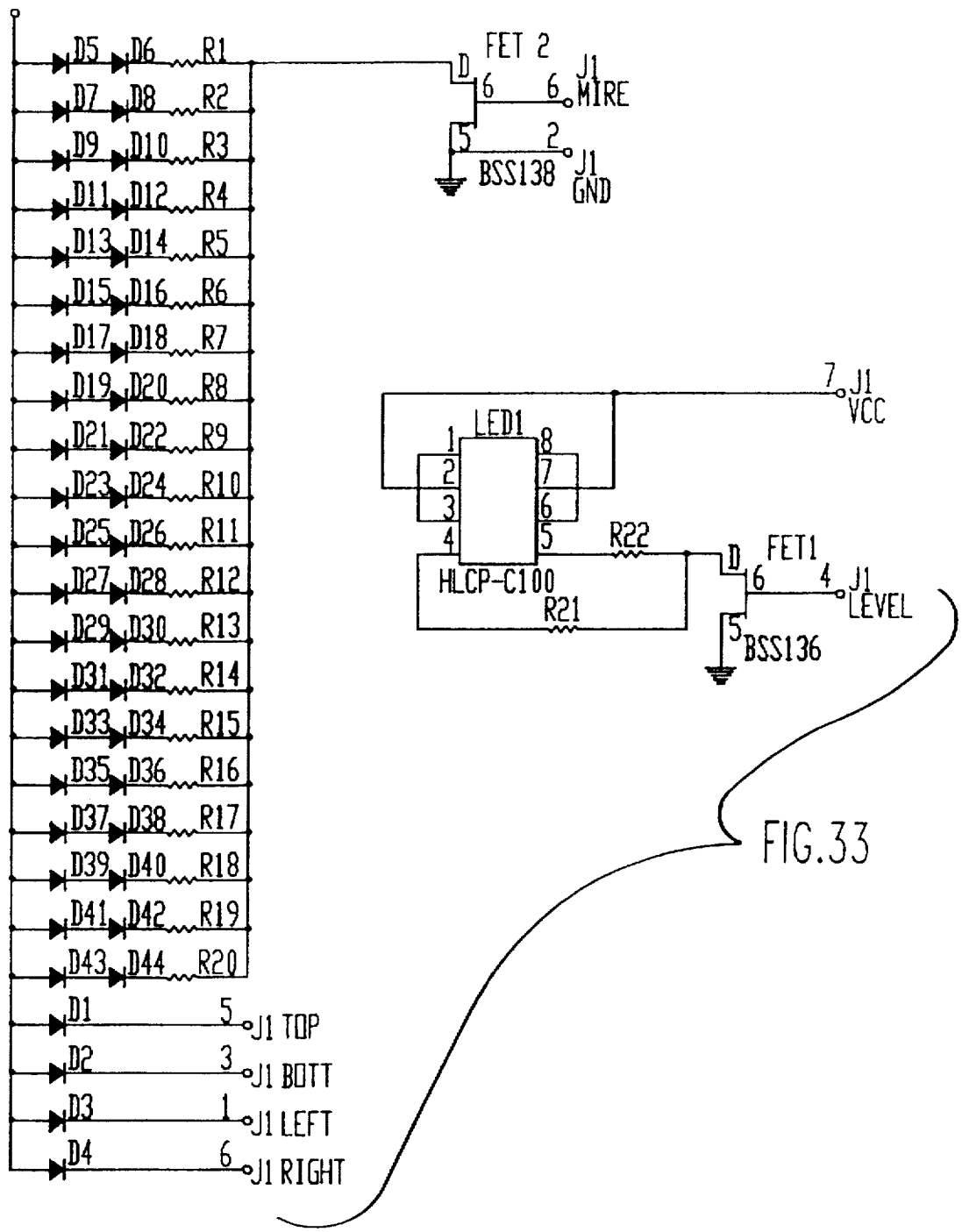
Figure 35:
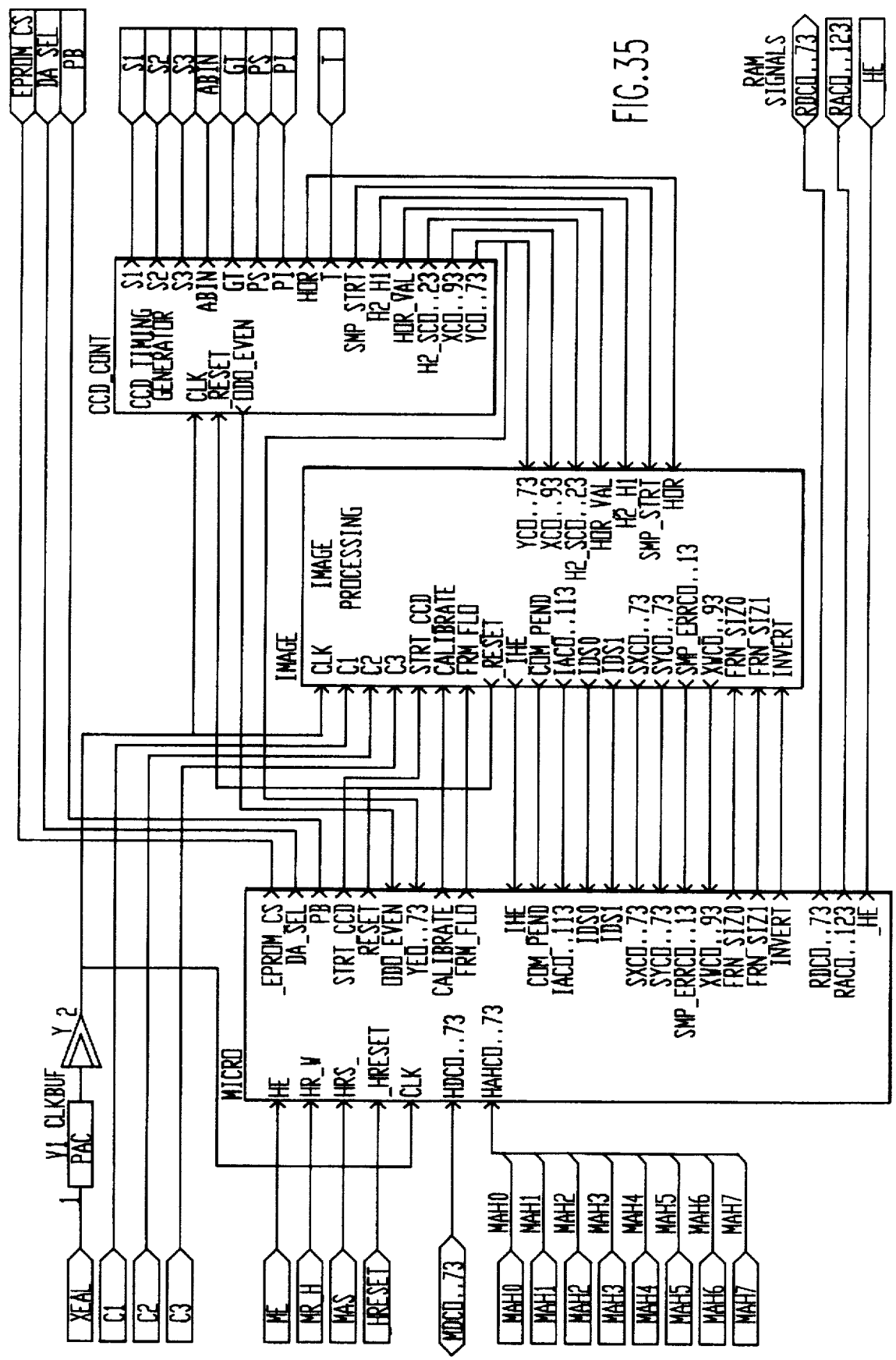
Figure 36:
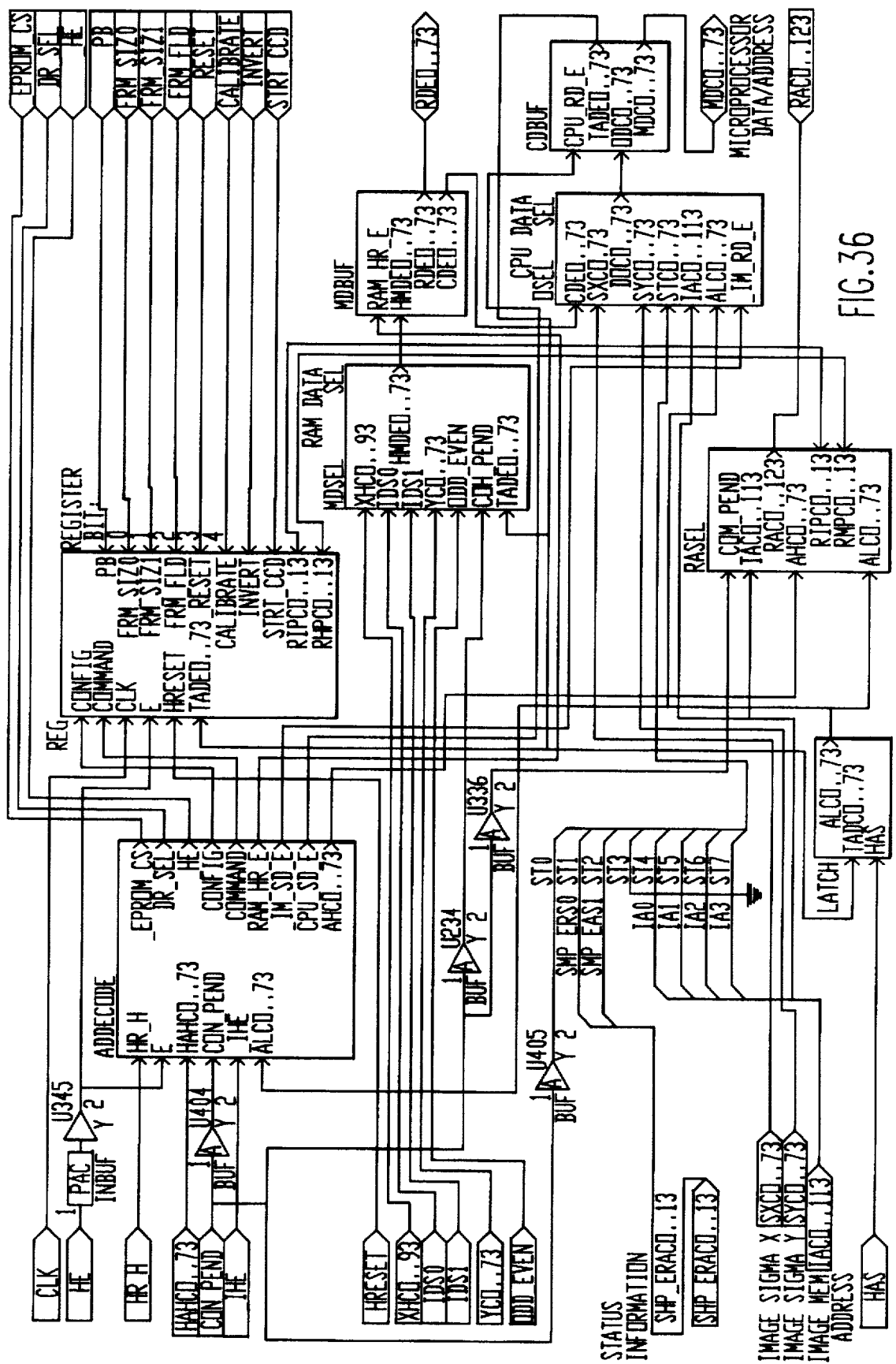
Figure 37:
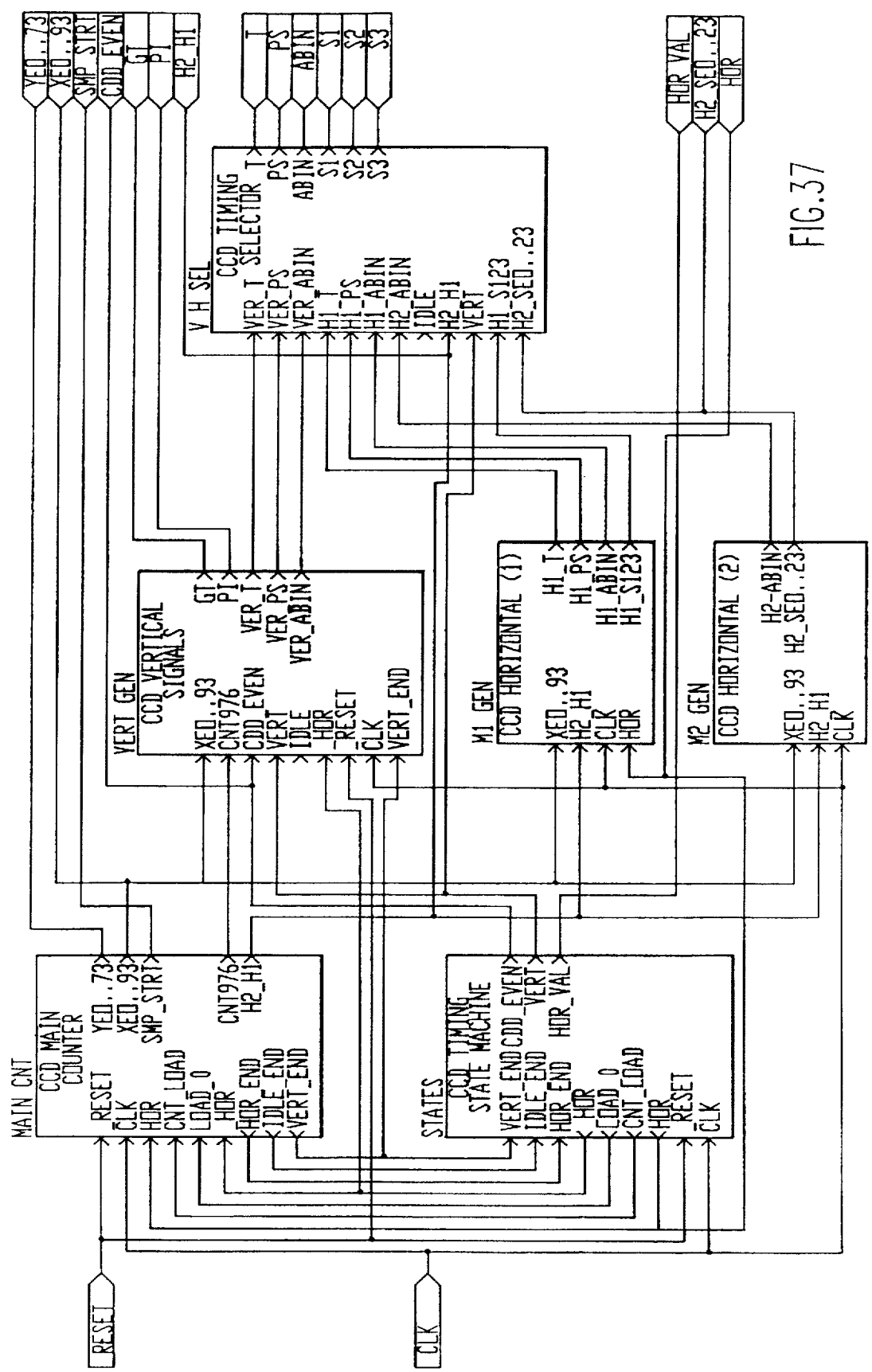
Figure 38:
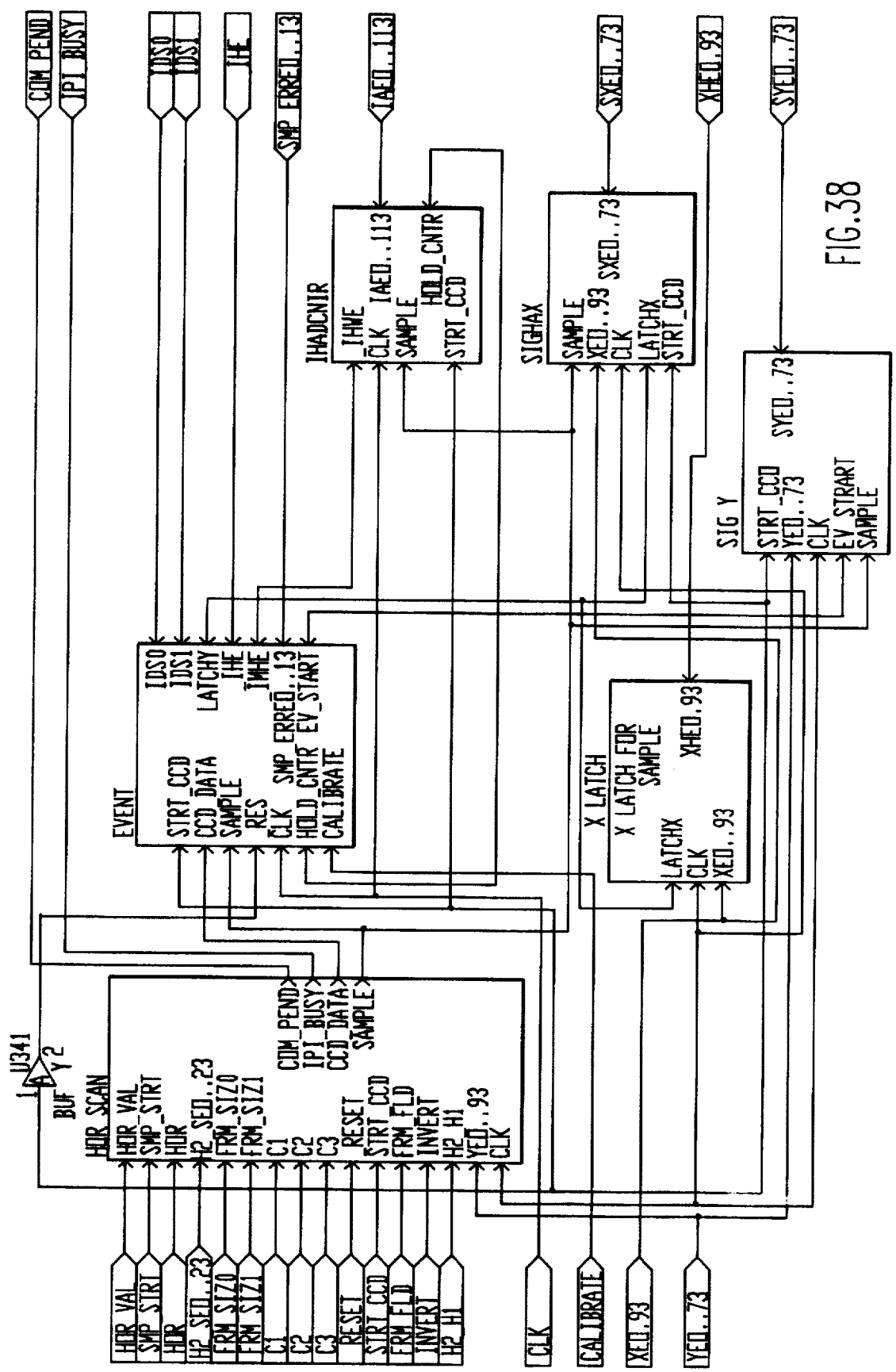

FIG. 33 is an electrical schematic of a Mire ring printed circuit board that can be used with the preferred embodiment of the invention.

FIGS. 34A-34B are diagrammatical charts of the different main function states for the software of the preferred embodiment of the invention.

FIGS. 35-38 are electrical schematics of the circuitry associated with image processing for the preferred embodiment of the invention.

IV. DETAILED DESCRIPTION OF THE PREFERRED EMBODIMENT

One preferred embodiment of the invention will now be described to assist in providing a more complete understanding of the invention. The description of this embodiment will be in detail including various features and advantages which may accompany this embodiment. The invention is capable of taking on many different forms and embodiments. This is but one of those forms, and is the preferred form.

This description will first give a broad overview of the embodiment and its structure. A more specific discussion of the structure will then follow. A description of the optical system of the embodiment will be set forth including examples of its operation. Finally, discussion of the electronic circuitry involved in the embodiment will be set forth referring to block diagrams and schematics.

This description is made in conjunction with the drawings. Reference numerals are sometimes utilized in the drawings to indicate specific parts and locations in the drawings. The same reference numerals will indicate the same parts or locations throughout all of the drawings, unless otherwise noted.

A. Overview

FIG. 1

FIG. 1 depicts in perspective keratometer 10 according to the present invention. Keratometer 10 includes a hand grip 12 at one end, and a projection portion 14 at the other end. An intermediate portion 16 exists between hand grip 12 and projection portion 14.

FIG. 1 illustrates keratometer 10 mounted in a base 18. Base 18 serves as a support stand for keratometer 10, and can also provide a connection to recharging circuitry to recharge the batteries which power keratometer 10. Further, as diagrammatically depicted in FIG. 1, base 18 can include connection means to auxiliary devices such as printer 20 or computer 22.

Hand grip 12, projection portion 14, and intermediate portion 16 comprise a housing 24 for keratometer 10. Dimensions of housing 24, for the preferred embodiment, are generally about 10-12 inches long, 3½ inches at its widest point, and about 3½ inches deep. It weighs only about 24 ounces. By gripping hand grip 12 (5 inches tall by 1¹⁵⁄₁₆ inches width and depth) and removing keratometer 10 from base 18, the keratometer 10 can be easily manipulated and moved with the operator. It also can be oriented easily in a number of different ways. This ability differs drastically from state of the art and is extremely advantageous.

Base 18, therefore, is only several inches long and wide. It takes up a very small "footprint" on a table or a cabinet top in comparison to present automated keratometers. It provides a secure and stable resting or storage place for keratometer 10, and allows the user to easily and quickly grab keratometer 10 and move it where the patient is, instead of requiring the patient to come to the machine and be manipulated into position.

Printer 20 allows readings obtained by keratometer 10 to be printed in hard copy. Printer could optionally be incorporated into base 18. The readings can then be preserved, for example, by immediately placing them in a patient's file. Computer 22 can be utilized to store measurements obtained by keratometer 10, or to program the operation of keratometer 10. Buttons 26 and 28 on the top face of base 18 can be utilized to control various operations as desired.

FIG. 1 also shows the basic structure of keratometer 10. This will be described further below, hand grip 12 would enclose a substantial amount of the electrical circuitry for keratometer 10. Intermediate portion 16 includes external control buttons 30 and display 32. Display 32 is a liquid crystal display (LCD) which is a reliable yet low power display.

Intermediate portion 16 and projection portion 14 contain most of the optical components for keratometer 10. FIG. 1 shows eye piece 34 which allows the user to view directly through projection portion 14 and out a projection window 36 on the opposite side. The user or operator of keratometer 10 would then hold housing 24 so that the projection window 36 is in front of and within a few inches of a patient's eye, while the users' eye is moved directly up to eye piece 34. This arrangement is easily facilitated by the shape and configuration of housing 24, including hand grip 12. The user's thumb can easily push any of the control buttons 30 or fingers on the other hand of the user can also do the same. The user does not have to move very much to check the display window 32.

FIG. 2

FIG. 2 shows keratometer 10 and base 18 from a different angle in a slightly enlarged form. A socket 38 exists in base 18 to receive end 40 of hand grip 12. A mating connection 42 inside base 18 allows electrical communication between keratometer 10 and base 18 to in turn facilitate connection to recharger, printer 20, or computer 22.

A spine 44 extends from the rear of base 18 vertically upwardly. An extension 46 consisting of a bent rod extends from spine 44 outwardly and upwardly to a top end 48. A notch 50 in the underside of projection portion 14 of keratometer 10 is configured to matingly settle on top end 48 when keratometer 10 is placed on base 18 as shown in FIG. 2. This securely and stably holds keratometer 10 in place.

Base 18 includes a circuit board 52 (see FIGS. 30A & 30B) which can contain the interface between keratometer 10 and printer 20 or computer 22. Base 18 could contain an LED light or lights 54, if desired, to indicate recharging or printer in use, or other matters, as desired.

B. Overview of Operation

A basic simplified description of operation of keratometer 10 will now be described with reference to FIGS. 1 and 2. Keratometer 10 is used to measure at least two radii of curvature of a patient's eye. These radii of curvature are usually taken along axes which are perpendicular to one another and which intersect at or near the optical center of the eye (generally the center of the cornea). If these radii of curvature are known, the diopter power or refractive power of the eye can be calculated. Keratometer 10, therefore, basically is measuring the refractive power of the eye. It is a diagnostic tool to understand what type of correction the eye might need in the form of eye glasses or contacts or the type of fitting needed. It also may be used to discern any deformities or other problems with the eye.

The preferred embodiment of keratometer 10 allows the user to easily and quickly pick up keratometer 10, move it up to the patient's eye, align the keratometer, and take the appropriate measurements. When the readings are complete, they are stored and can be displayed on display 32. They can then be printed out to printer 20 when keratometer 10 is replaced to base 18.

In very simplistic terms, the measurements are taken as follows. The user brings keratometer 10 into position a few inches or centimeters from the patient's eye. The user then looks through eye piece 34 and can clearly see the patient's eye. The user then tries to center keratometer 10 with respect to the patient's eye by estimation but is assisted in this because eye 34 is positioned directly along an axis which becomes co-linear with an optical axis extending through eyepiece 34 and projection window 36. In other words, if a line were drawn through the center of eye piece 34 and out the center of projection window 36, the user would try to put that line directly on the middle of the cornea of the patient's eye (or some other aiming point on the eye).

Keratometer 10 includes automated methods to confirm centering of the keratometer 10, as well as to make sure that it is not too far away or too close to the patient's eye. A significant advantage of the present invention is that it does not require exact axial positioning of keratometer 10 with respect to the patient's eye but only requires that it be within a certain range of positions which can be verified by the machine.

Alignment is facilitated by projecting a pattern of collimated light sources onto the eye. The pattern is configured so that the operator, by viewing the reflection of the pattern through the eye piece can tell if keratometer 10 is within correct range from the patient's eye.

Once alignment is within an acceptable range, the actual measurements are taken generally as follows. A light is projected along the optical axes out the center of the projection window 36 onto the patient's eye.

This light serves as a fixation target for the patient to hold his/her eye steady. This fixation light is also visible by the user through eye piece 34 to assist in aligning the fixating light onto the patient's eye.

The next step is the projection of four highly collimated light sources onto the eye. These basically thin lines or beams of light converge at angles towards the optical axis and intersect the curved surface of the eye at points surrounding the fixation light along the optical axis.

Because the angles of these light beams is known with respect to the optical axis, measurement of the spacing of the light point images reflected from the cornea can be used to derive the radii of curvature and major and minor axis angles of the cornea.

Measurement of these distances is accomplished automatically. The reflection of the projected lights is received back through the projection window 36 and reflected along an optical axis to a camera which includes what is called a CCD imager. The imager is basically a matrix of picture elements (pixels) of very small size. Each pixel produces an electrical signal proportional to the intensity of light incident upon it and therefore basically replicates the reflection of the eye as it is received. The spacial positions of each pixel are known and correlated in memory and therefore distances between the reflected images of the projected lights can be derived electronically. The processor within keratometer 10 controls and calculates these measurements and converts them into readings which are displayed on display 32 and stored in memory.

Not only is keratometer 10 easy to handle, maneuver and use, it also facilitates quick and reliable accurate readings which can be preserved. The whole measurement process, including positioning of the patient, takes only a matter of seconds. It is fast enough that several readings can be taken and averaged to increase accuracy.

The structure and form of housing 24, along with its light weight, make it very ergonomic, in addition to providing the many advantages discussed. The operator can quickly and easily bring the keratometer to the patient, align it with automatic and automated assistance, verify the patient is fixated, and take the measurement automatically. This in turn makes it much easier for keratometric readings to be routinely taken by staff, which would require much less training and expertise than existing devices.

C. Detailed Structure

FIG. 3

Figure 3:
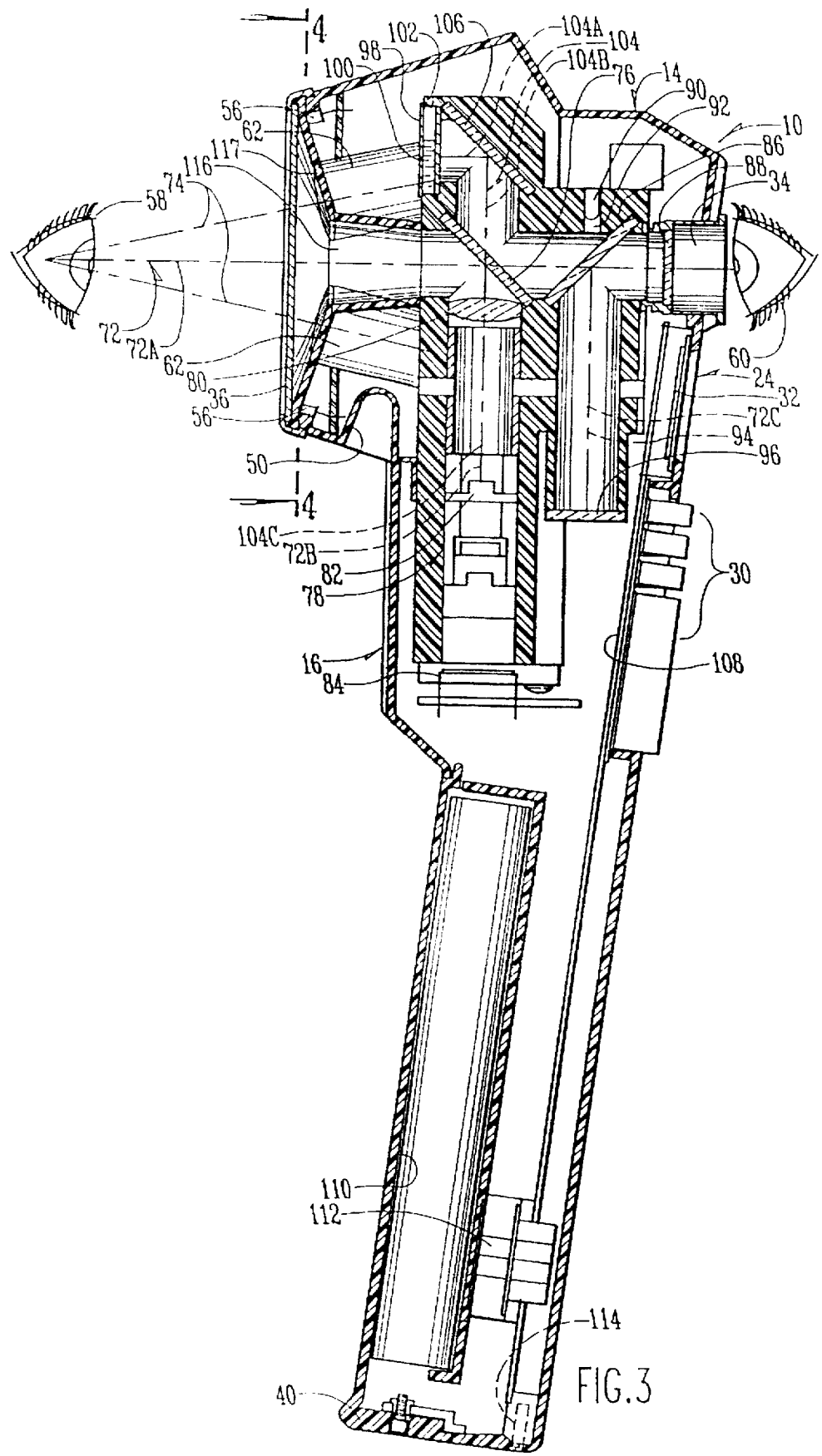
FIG. 3 is a still further enlarged sectional view taken along line 3—3 of FIG. 1.

FIG. 3 shows a still further enlarged form keratometer 10 in elevated section (and without base 18). The specific structure of the interior of housing 24 is shown. Projection window 36 is a plat glass disc (Rolyn Optics, Part #55.1258, 47.6 mm dia., 3.1 mm thick). Behind window 36 are a ring of red LEDs 56 (see also FIG. 4) around the outer circumferential edge of window 36. These LEDs are angularly oriented in converging fashion and when powered simultaneously project a ring of red light onto a patient's eye (depicted at 58 in FIG. 3). The ring of light is called a mire ring which when projected on eye 58 allows the user (see user's eye 60 in FIG. 3) to look through eye piece 34, and see the ring on eye 58 to subjectively determine if there are any abnormalities in the curvature or roundness of the eye.

Also behind window 36 are the four projectors 62 which project the thin collimated light beams onto the eye. Each projector consists of an LED 64 (Hewlett-Packard Part #HLMP-Q101, T 1 ¾ red tinted diffused LED) behind a pinhole card 66 (1 mm pinhole) and a compound collimating lens 68 (Edmund Scientific B32, 719 Achromat, 30 mm focal length, 15 mm dia. +/−0.1 mm). These components are held in projector tubes 70 which are each oriented at 21.5° (+/−1°) with respect to optical axis 72 as shown in FIG. 3. Projector 62 therefore projects a point source of light along axes 74 so that they intersect with optical axis 72. By referring to FIG. 4, it can be seen that each projector tube 70 is spaced an equal radial distance from optical axis 72 and at 90° from one another circumferentially around optical axis 72. As can be appreciated in FIG. 3, the patient's eye 58 must therefore be positioned in front of the point of intersection of axes 74 with optical axis 72 so that each point of light from projectors 62 will be spaced apart on the front surface of eye 58. However, it is to be understood that there is a range of positions for eye 58 along axis 72 which allow reliable readings to be taken and therefore exact positioning is not required.

The optical axis of keratometer 10 consists of portion 72a extending through eye 58 and originating inside housing 24. Portion 72b reflects off beam splitter 76 downwardly in FIG. 3 to camera means 78. Camera means 78 includes a compound lens 80 (Edmund Scientific Part #B32, 312 Achromat Objective Lens, 35 mm f.l., 12.5 mm dia, +/−0.1 mm), a pinhole device 82 (telocentric aperture pinhole −0.36 mm dia., C.A.), and an imaging device 84 (Texas Instruments TC 245, CCD Image Sensor). Camera means 78 captures the image of eye 58 and any projected beams onto eye 58 and electronically records those images. In the preferred embodiment, imaging device 84 is a CCD photo sensitive electronic area imager, such as is known in the art.

FIG. 3 shows that portion 72c of optical axis 72 allows light to pass through beam splitter 76 and beam splitter 86 into eye piece 34. The user can then directly view the patient's eye 58 along the optical axis 72. Eye piece 34 includes a lens 88.

FIG. 3 also shows additional optical components of preferred embodiment 10. A fixation LED 90 directs light from aperture 92 onto beam splitter 86. Beam splitter 86 allows some of the light to travel directly downward along axis 94 to a mirror 96. The light is then reflected back to beam splitter 86 which reflects some of the light along axis 72c to the user's eye 60. Beam splitter 86 directs another portion of the light from fixation LED 90 along axis 72c between beam splitter 86 and 76, through beam splitter 76 along axis 72a to the patient's eye 58. The fixation LED 90 therefore presents a perceivable image along optical axis 72 for the patient to fixate on. This means the patient will concentrate on looking directly at the light, not moving the eye, and not moving the head. Additionally, the projection of fixation LED 90 a distance down axis 94 to mirror 96 and back to eye piece 34 is done for the following reasons. The optical path distance between LED 90 and eye piece 34 is generally equal to the distance from the patient's eye 58 to eyepiece 34. The user will therefore perceive the image of the LED 90 to be approximately superimposed upon user's eye 60. The patient will perceive the LED image to be approximately 10 cm in front of his/her eye 58. Therefore, this arrangement gives the user a virtual image of LED 90 directly along the appropriate optical axis so that keratometer 10 can be accurately positioned with respect to the patient's eye 58.

A leveling system is incorporated into the keratometer 10 to automatically indicate the housing 24 is being held generally vertically straight up and down. A small rectangular sealed container 98 is filled partially with fluid such as oil (for example, baby oil). An LED 102 illuminates the oil in container 98, essentially back-lighting the container 98 and oil 100, including the meniscus formed at the top of the fluid in the container. The image of container 98 can travel along axis 104 portions a, b and c reflecting off of mirror 106 traveling through beam splitter 76 to camera means 78. By discerning the meniscus line between the top of oil 100 and the rest of container 98, it can be determined if housing 24 is correctly vertically positioned. It does not indicate whether housing 24 is tilted too far towards or away from the patient's eye 58, however. This alignment problem is solved by other means which will be discussed later.

FIG. 3 also shows how housing 24 contains a printed circuit board 108 which extends virtually from the lower end 40 of housing 24 through handle grip 12, intermediate portion 16, and into projection portion 14. The battery compartment 110 is also shown. In the preferred embodiment, four AA batteries are utilized to power keratometer 10. An interface between battery compartment 10 and circuit board 108 (denoted by number 112) is also shown. Contacts 114 between circuit board 108 and the end 40 of hand-grip 12 are shown which provide the communication between base 18 and keratometer 10.

FIG. 4

Figure 4:
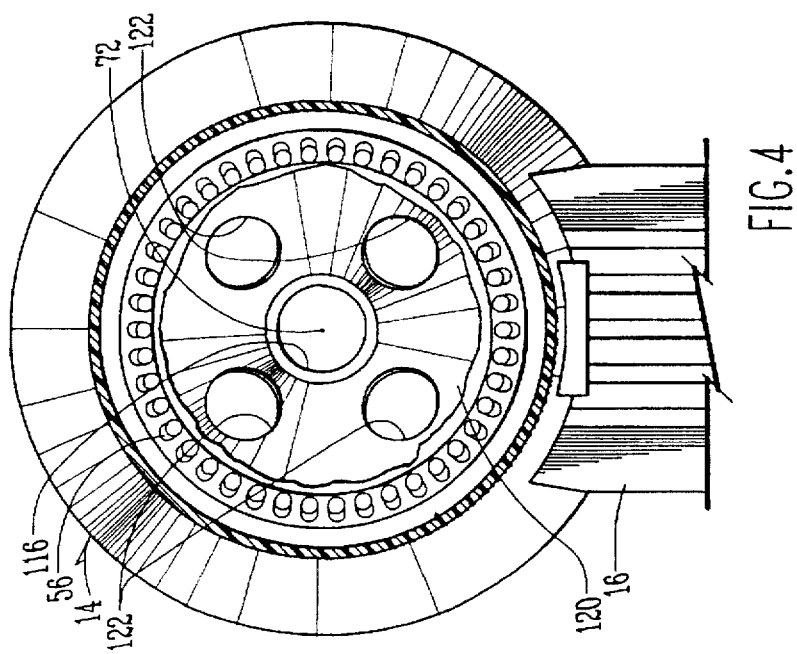
FIG. 4 is a partial section, partial cutaway view, taken generally along line 4—4 of FIG. 3.

FIG. 4 generally depicts the side of keratometer 10 which is positioned in front of patient's eye 58. Axis 72 is directed toward the center of patient's eye 58, and the ends of projector tube 70 will issue the collimated light sources onto patient's eye 58. Aperture 116 is formed in a support 117 in housing 24, and represents the opening through which the reflection from the patient's eye 58 returns along optical axis 72 into keratometer 10.

FIG. 5

Figure 5:
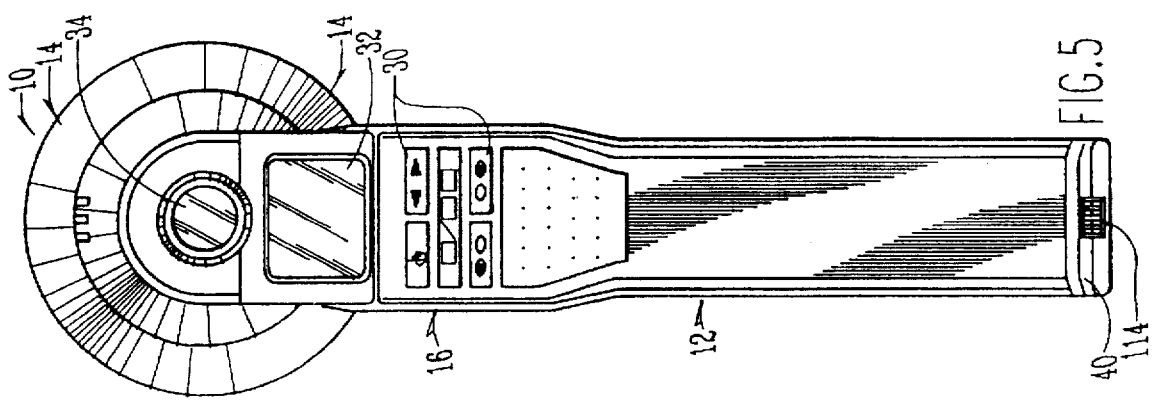
FIG. 5 is an enlarged front elevational view of FIG. 1.

FIG. 5 depicts the side of keratometer 10 which includes eye piece 34 and control buttons 30. Display 32 is also shown along with connection 42 at the lower end of handgrip 12. Control buttons 30 can be for different desired functions or operations. In the preferred embodiments, buttons 30 relate to such things as selection of right or left eye of a patient, or measurement and storage of readings.

FIG. 6

Figure 6:
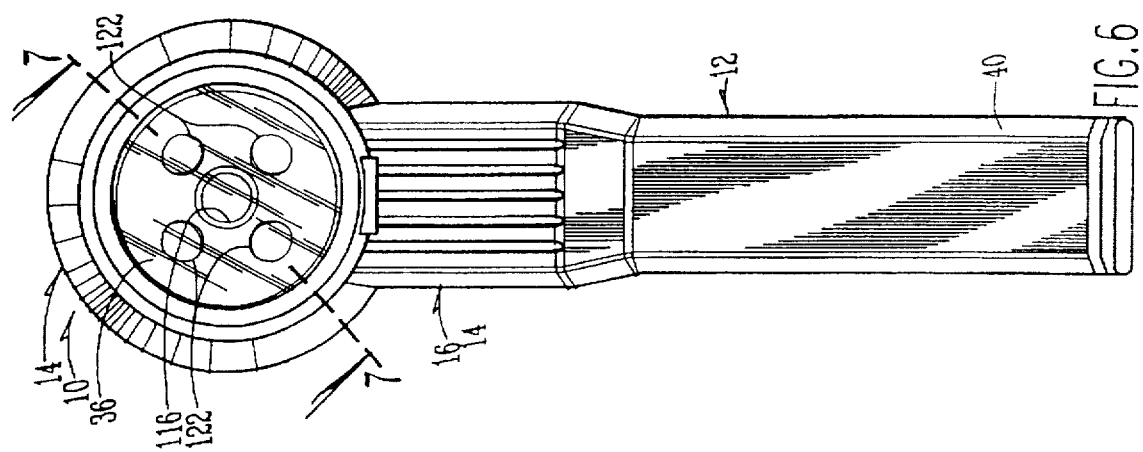
FIG. 6 is an enlarged back elevational view of FIG. 1.

FIG. 6 shows the opposite side of keratometer 10, similar to FIG. 4.

FIG. 7

FIG. 7 is a sectional view of the interior of projection portion 14. It shows in more detail each projector 62 according to the present invention. In particular, it shows each projector tube 70 is slightly adjustable along projector base 118. This allows a slight adjustment of lens 68 with respect to pinhole card 66 and LED 64. It is also noted that internal support 117 of housing 24 include apertures 122 along axes 74 to allow passage of the collimated light source from projector 62.

Still further, FIG. 7 illustrates that additional LEDs 124 and 126 (Hewlett-Packard Part #HLMP-7040 Green tinted, low current) can be positioned on opposite sides of LED 64 in each projector 62. Because LEDs 124 and 126 are basically in the same plane as LED 64, but are on either side of LED 64, the collimated light beams from these LEDs reaching the patient's eye 58 will cross the optical axis 72 at different angles and distances than the beam from LED 64.

FIG. 8

By referring to FIG. 8, a front view of the projector 62 is shown, which reveals the positions of LEDs 64, 124, and 126. In the preferred embodiment, LEDs 124 and 126 are green LEDs, whereas LED 64 is red.

FIGS. 9, 10, 11

Figure 10:
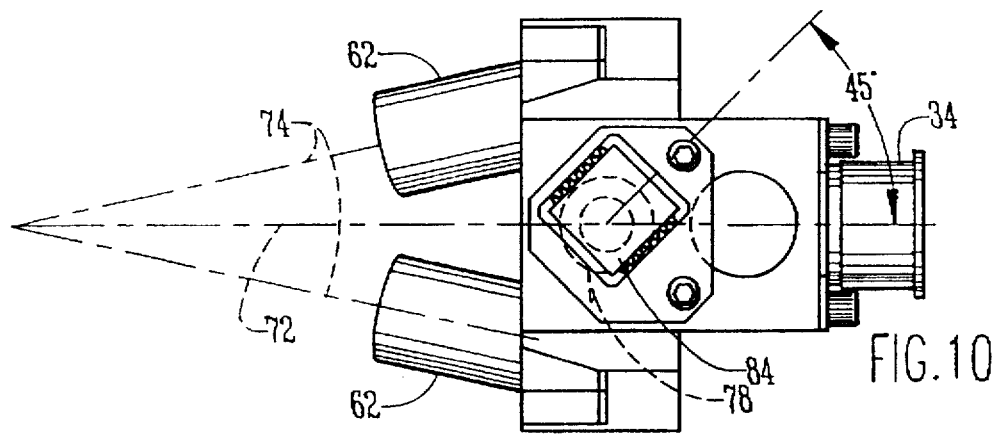
FIG. 10 is a bottom plan view of FIG. 9.
Figure 11:
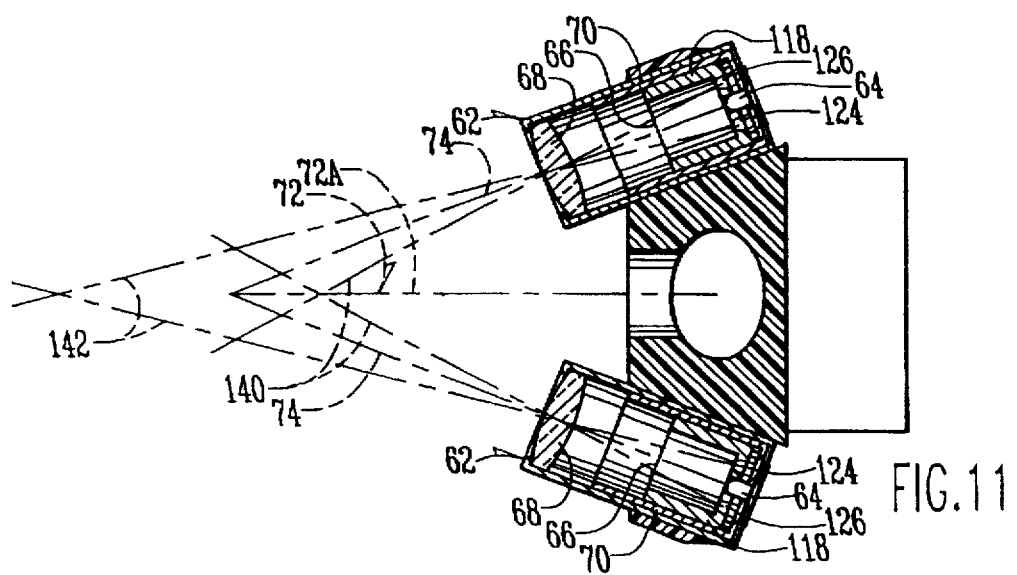
FIG. 11 is an isolated enlarged depiction of two projection means according to FIGS. 9 and 10 and the preferred embodiment of the invention.

FIGS. 9, 10 and 11 show the optical system of the present invention in more isolated fashion. FIG. 9 is similar to FIG. 3. FIG. 11 is similar to FIG. 7. FIG. 10, however, shows how the imaging device 84 is positioned basically at a 45° angle to optical axis 74. Therefore, its basically rectangular pixel array is also rotated 45° with respect to the optic axis. Note particularly how lines 140 from LEDs 126 and lines 142 from LEDs 124 in FIG. 11 show how collimated light from the different LEDs will intersect optical axis 72 at different points.

FIG. 12

Figure 12:
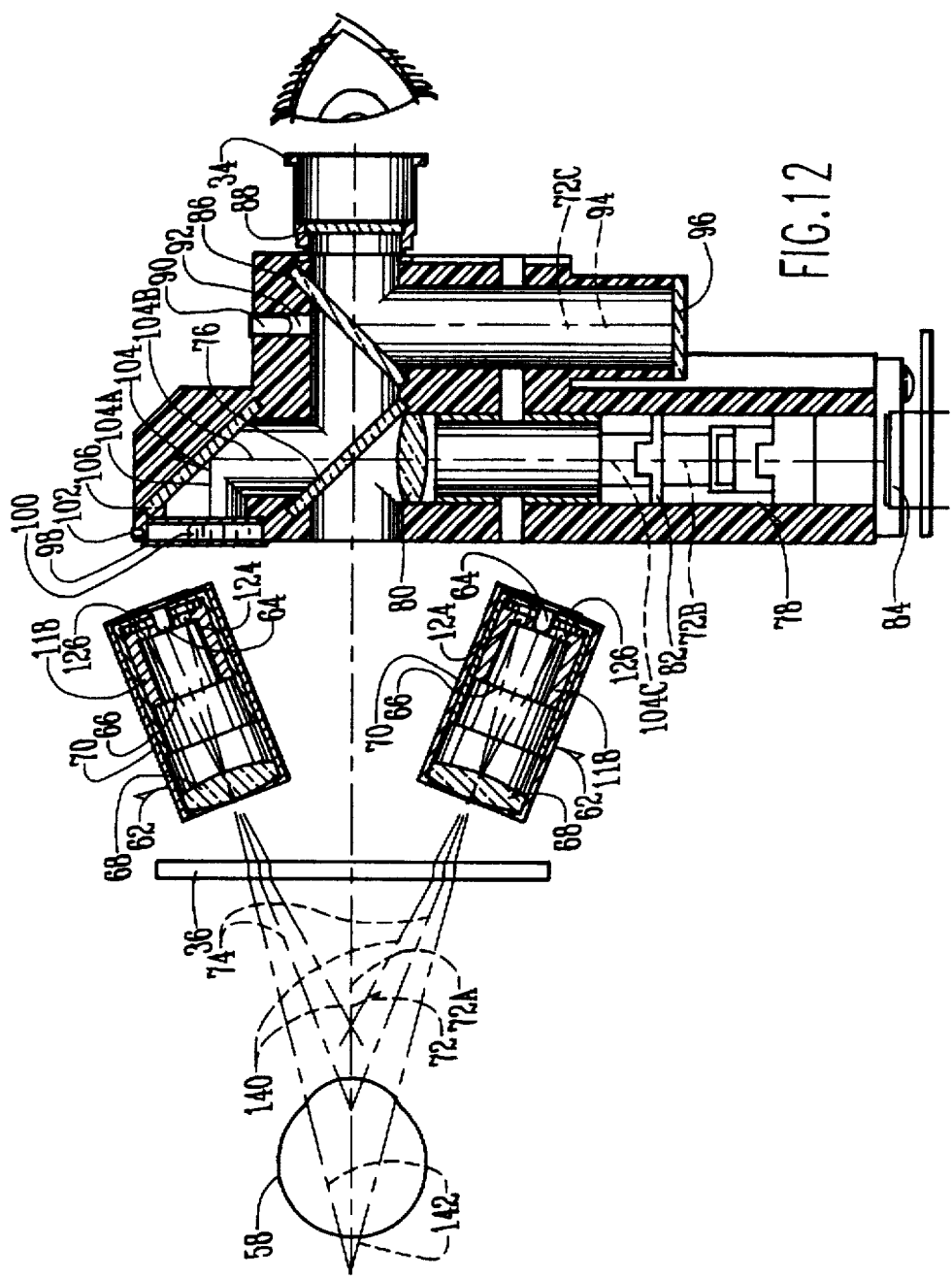
FIG. 12 is a diagrammatic view of the optical system of the preferred embodiment of the invention.

FIG. 12 shows in diagrammatic form the optical system of the present invention including relative distances between components, and the effects of the various optical features on the optical pathways. In particular, FIG. 12 illustrates how the collimated light sources 64, 124 and 126 project onto the patient's eye 58.

FIG. 13

FIGS. 13A–D diagrammatically depict a patient's eye 58. Eyeball 188 contains a cornea 190 which is generally circular in shape. The preferred embodiment of keratometer 10 imposes four LED collimated light beams 64 onto eye 58. The instrument is calibrated by measuring the position of the reflected images (200a–d) from each collimated LED light beam using a reference sphere in place of the cornea. This calibration measurement as well as subsequent corneal measurements are made using the CCD imager and its associated telocentric objective lens. The spot positions measured by reflection from the cornea and the calibration spot positions are used to compute the corneal curvature along the axis of maximum curvature, the corneal curvature along the axis of minimum curvature, and the angles that each curvature axis makes with respect to horizontal. The measurement can be made using a minimum of three spots. However, accuracy is increased when four spots are used. In addition, when four spots are used the instrument can detect that the corneal surface has a nontoric component of curvature. FIGS. 13A and 13B depict measurement where the spots 200a–d are centered at the center of the cornea for central corneal Keratometer readings. FIGS. 13C and 13D show the spots 200a–d off the center of the cornea for peripheral Keratometer readings.

FIGS. 14A–G

FIG. 14A–G depict diagrammatically various situations which can occur with keratometer 10 as seen through eye piece 34. FIG. 14a shows how fixation beam 202 can be projected and housing 24 moved to center it on cornea 190. FIG. 14b illustrates first how LEDs 56 can impose the mire ring 57 of light on eye 58. It also shows that if all LEDs 64, 124 and 126 are turned on, as well as fixation LED 90, the type of pattern that is shown on eye 58 if correctly aligned. It can be seen that red LED 64 spots 200a–d surround fixation LED spot 202.

It can be seen that the red LED's 64 form a pattern surrounding the perimeter of the red fixation LED which is generally centered along optic axis 72. Note also that the green alignment LED's (spots 201a–d) form a similar pattern on a circle of larger radius, and green alignment LED's (spots 202 a–d) form a similar pattern on a circle of smaller radius.

FIG. 14C indicates keratometer 10 is too close to the patient's eye 58. It indicates that only the outer green LED's (spots 201a–d) can be seen and neither the red LED's 64 (spots 200 a–d) nor the inner green LED's (spots 202 a–d) can be seen.

FIG. 14D indicates keratometer 10 is too far from the patient's eye 58. It indicates that only the inner green LED's (spots 202a–d) can be seen and neither the red LEDs 64 (spots 200a–d) nor outer green LEDs (spots 201a–d) can be seen.

FIG. 14E illustrates fixation point 202 off center.

FIG. 14F shows when the patient is not fixating on the red fixation LED 202.

FIG. 14G is a depiction of operation of keratometer 10 once green and red LED spots have been used to align keratometer 10 with respect to the patient's eye 58 (as shown in FIG. 14B). In the preferred embodiment, at this point, the control circuitry of keratometer 10 would turn off the green LEDs 124 and 126 (illustrated by "X"'s) leaving only the red LEDs 64 and the center red fixation LED 202.

FIG. 15

It is to be understood that the camera means would basically capture what corresponds to FIGS. 14A through 14G.

It should be remembered that the basically rectangular matrix of pixel cells of the CCD imager of the camera means is rotated 45° with respect to optical axis 72. The images captured by the camera means therefore are rotated 45° to correspond with the images shown in FIGS. 14A–G.

FIG. 15 depicts a centered pattern of red LEDs ready for measurement, corresponding to the pattern as shown in FIG. 14G. As has previously been explained, the two dimensional capturing of the image of FIG. 15 allows the processor to know the relative distances between the four red spots 200a–d; in turn allowing it to use algorithms calibration spot position data and mathematical calculations to derive the radii of curvature and axis angles previously explained.

FIG. 16

FIGS. 16A–16C set forth a flow chart of the software operational steps of the preferred embodiment of the present invention.

FIG. 17

FIGS. 17–24 depict the main electrical circuitry of the preferred embodiment. This circuity exists inside housing 24 primarily on PC board 108.

FIG. 17 shows block diagram of the two main sections of the circuit board 108 of keratometer 10, namely, the main board 302 and an input/output section 304.

FIG. 18

FIG. 18 shows a partial diagrammatic and partial schematic view of the input/output section 304 circuit board 108, including the keyboard section 306 which relates to the control button the LED's of keratometer 10.

FIG. 17 shows that i/o section 304 includes an LCD display 308, the keyboard section 306 and LED outputs 310. Main board 302 includes a DC/DC Converter 312, micro processor 314, image processors 316, and CCD interface 318.

FIG. 18 more specifically shows that i/o section 304 contains the LCD display 308 and the driving circuitry for back light LEDs 320, to back light the LCD display. It also includes LED drivers 322 to drive the various LEDs to the system. A keyboard interface 324 allows interaction of the actual keyboards which is 306 (see switches S1–S15) with the circuitry. Additionally a beeper driver 326 is used to operate a transducer which issues an audible signal to the operator, according to software.

FIG. 18 illustrates the inter connections it would have with other components, for example input/output connections 328 would communicate with the main board 302. Header 330 connects the LED drivers 322 to the actual LEDs.

FIG. 19

FIG. 19 shows in detailed electrical schematic i/o section 304.

FIG. 20

FIG. 20 shows in block diagram form the contents of the main board 302.

It can be seen how micro processor 314 communicated with image processor 316, which in turn is communicated to CCD interface 318. FIG. 20 also shows the inner connections of micro processor 314 with i/o section 304 at reference numeral 332. Headers 334 and 336 comprise the communication between keratometer 10 and base 18. Header 338 communicates the image processor 316 and CCD interface 318 with the CCD imager 84.

FIG. 21

FIG. 21 shows in detailed electrical schematic CCD driver section 318 of the main board.

FIG. 22

FIG. 22 shows in detailed electrical schematic the power supply circuit 312 for keratometer 10.

FIG. 23

FIG. 23 shows in detailed electrical schematic micro-processor 318 for the main board 318.

FIG. 24

FIG. 24 shows in detailed electrical schematic the image processor circuit 316 of the main board 318.

To allow a more complete understanding of the preferred embodiment of the invention, below is a detailed description of the electrical circuits previously identified and shown in the drawings, as well as the operation of that circuitry.

FIG. 25

FIG. 25 is a general block diagram of the overall circuitry of the preferred embodiment. Reference to FIG. 25 will assist in understanding the sections and interconnection of sections of the circuitry, as well as be a helpful reference when reading the detailed description of the operation of hardware and software, which follows.

FIGS. 26–27

These figures are block diagrams of the imaging processing parts of the circuitry and will assist in an understanding of this part of the invention.

FIGS. 28–33

These figures supplement the main electrical schematics and depict various electrical circuits and boards that can be used with the preferred embodiment.

FIGS. 34A–34B This chart is helpful in understanding the software operation of the preferred embodiment. FIGS. 34A and 34B are on a chart which should be read from bottom to top of FIG. 34A and then bottom to top of FIG. 34B.

FIGS. 35–38

These electrical schematics show details of the image processing circuitry and should be referenced particularly with Section F entitled "Image Processing Algerithm", and following Section G.

In the following section D, entitled "Electronic Circuit Operation", and Section E entitled "Keratometer Operation", references to sheets 1–8 corresponds as follows to FIGS. 17–24 of the drawings.

| SHEET | FIG. |
| --- | --- |
| 1 | 17 |
| 2 | 18 |
| 3 | 19 |
| 4 | 20 |
| 5 | 22 |
| 6 | 24 |
| 7 | 21 |
| 8 | 23 |

It can therefore be seen that the present invention, in its preferred embodiment, achieves at least all the inventions stated objectives. The invention can take many forms and embodiments. The preferred embodiment is given by way of example only, and not by way of limitation to the invention. The true essence and spirit of this invention are defined in the appended claims, and it is not intended that the embodiment of the invention presented herein should limit the scope thereof.

As a primary example, the present invention can be utilized to determine the curvature of any curved surface which allows reflection to the extent needed for the image processing to function. The device therefore could be utilized to, for example, insure that field ball bearings are being manufactured to the required specifications.

Other uses are possible. Additionally, other features, additions, and enhancements are possible.

What is claimed is:

1. A hand held keratometer comprising:
    at least two collimated light sources, said light sources being located in a plane substantially perpendicular to an optical axis and being focused to converge at a single point on said optical axis;
    a camera telecentrically aligned with said optical axis to receive reflections of light from said light sources reflecting from a patient's eye located in and generally coaxially aligned with said optical axis; and
    a portable housing including a hand grip, said housing enclosing said light sources and said camera.

2. The keratometer of claim 1 further comprising a plurality of light sources for projection of light onto the patient's eye for alignment of the keratometer therewith.

3. The keratometer of claim 2 further comprising a processor connected to said camera for processing information relating to said received reflected light and determining keratometric data therefrom.

4. The keratometer of claim 3 wherein said processor includes means for determining when said keratometer is aligned with said patient's eye and means for automatically initiating a measurement of the eye in response to said alignment determining means.

5. The keratometer of claim 4 further comprising a fixation target projected along said optical axis and viewable by said patient's eye to assist in aligning said patient's eye along said optical axis.

6. The keratometer of claim 5 further comprising a beam splitter located in said optical axis for diverting said reflected light into said camera, said camera being positioned at an angle to a portion of said optical axis extending between said patient's eye and said beam splitter.

7. The keratometer of claim 6 further comprising a view window physically aligned with said beam splitter and said patient's eye through which a user may sight the patient's eye during use.

8. The keratometer of claim 7 wherein the camera is a CCD imaging device.

9. The keratometer of claim 8 further comprising a display for displaying the measured keratometric data to the user.

10. A method of keratometry with a hand held keratometer comprising the steps of:

projecting a plurality of collimated light sources at generally equal converging angles onto a patient's eye;

substantially centering the light sources around an optical axis which extends through the center of the cornea of the eye and generally normal to the eye;

capturing along the optical axis a reflected image of the light sources from the eye; and deriving keratometric information from the captured reflected image;

and further comprising the steps of sensing the alignment of the keratometer with respect to the eye and automatically initiating the capture of a reflected image in response to the sensing of alignment.

11. The method according to claim 10 wherein light projected from the light sources converges to a point on the optical axis and the method further includes the step of positioning the keratometer so that the eye is nearer the light sources than the point.

12. The method according to claim 11 wherein the step of capturing the reflected image includes the step of capturing the reflected image with a CCD imager.

13. The method according to claim 12 further comprising the step of projecting a fixation image along the optical axis viewable by both the patient's eye and a user.

14. The method of claim 13 further comprising the step of contemporaneously storing and then displaying the keratometric information from a display in the keratometer.

15. A hand held keratometer comprising:

a collimated light source and a camera located within a hand-held, portable, battery powered housing such that the housing may be conveniently positioned in closed proximity to a person's eye;

the camera being located to receive and capture light beams from said collimated light source which are reflected off the eye; and a processor for converting the information relating to said captured light beams into keratometric readings;

wherein said collimated light source comprises a plurality of collimated light sources, all of which are focused at a point alone an optical axis, said camera being telecentrically aligned with said optical axis.

16. The keratometer of claim 15 wherein the camera includes a CCD imager to capture said reflective light beams.

17. The keratometer of claim 16 wherein said processor includes an image processor for simplifying the image data.

18. The keratometer of claim 17 wherein said processor includes means for converting multiple separate images of said captured light beams into multiple keratometric data and means for processing the multiple keratometric data to minimize noise therein.

19. A keratometer comprising:

at least two collimated light sources, said light sources being located in a plane substantially perpendicular to an optical axis and being focused to converge at a single point on said optical axis; and a camera telecentrically aligned with said optical axis to receive reflections of light from said light sources reflecting from a patient's eye located in and generally co-axially aligned with said optical axis.

20. The keratometer of claim 19 further comprising a plurality of light sources for projection of light onto the patient's eyes for alignment of the keratometer therewith.

21. The keratometer of claim 20 further comprising a processor connected to said camera for processing information relating to said received reflected light and determining keratometric data therefrom.

22. The keratometer of claim 21 wherein said processor includes means for determining when said keratometer is aligned with said patient's eye and means for automatically initiating a measurement of the eye in response to said alignment determining means.

23. The keratometer of claim 22 further comprising a fixation target projected along said optical axis and viewable by said patient's eye to assist in aligning said patient's eye along said optical axis.

24. The keratometer of claim 23 further comprising a beam splitter located in said optical axis for diverting said reflected light into said camera, said camera being positioned at an angle to a portion of said optical axis extending between said patient's eye and said beam splitter.

25. The keratometer of claim 24 further comprising a view window physically aligned with said beam splitter and said patient's eye through which a user may sight the patient's eye during use.

26. The keratometer of claim 25 wherein the camera is a CCD imaging device.

27. The keratometer of claim 26 further comprising a display for displaying the measured keratometric data to the user.

28. A method of keratometry comprising the steps of:

projecting a plurality of collimated light sources at generally equal converging angles onto a patient's eye;

substantially centering the light sources around an optical axis which extends through the center of the cornea of the eye and generally normal to the eye;

capturing along the optical axis a reflected image of the light sources from the eye; and deriving keratometric information from the captured reflected image; and further comprising the steps of sensing the alignment of the keratometer with respect to the eye and automatically initiating the capture of a reflected image in response to the sensing of alignment.

29. The method according to claim 28 wherein light projected from the light sources converges to a point on the optical axis and the method further includes the step of positioning the keratometer so that the eye is nearer the light sources than the point.

30. The method according to claim 29 wherein the step of capturing the reflected image includes the step of capturing the reflected image with a CCD imager.

31. The method according to claim 30 further comprising the step of projecting a fixation image along the optical axis viewable by both the patient's eye and a user.

32. The method of claim 31 further comprising the step of contemporaneously storing and then displaying the keratometric information from a display in the keratometer.

* * * * *